US008877198B2

(12) United States Patent
Cook et al.

(10) Patent No.: US 8,877,198 B2
(45) Date of Patent: Nov. 4, 2014

(54) METHODS OF REDUCING PHOSPHATE ABSORPTION

(75) Inventors: Mark Cook, Madison, WI (US); Martin Petkovich, Kingston (CA); Christian Helvig, Makham (FR); Erica Hellestad, Madison, WI (US); Keith Crawford, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1363 days.

(21) Appl. No.: 12/447,338

(22) PCT Filed: Oct. 23, 2007

(86) PCT No.: PCT/US2007/082244
§ 371 (c)(1),
(2), (4) Date: May 27, 2010

(87) PCT Pub. No.: WO2008/051977
PCT Pub. Date: May 2, 2008

(65) Prior Publication Data
US 2010/0233184 A1 Sep. 16, 2010

Related U.S. Application Data

(60) Provisional application No. 60/854,550, filed on Oct. 26, 2006.

(51) Int. Cl.
*A61K 39/395* (2006.01)
*C07K 16/40* (2006.01)
*A61K 39/00* (2006.01)

(52) U.S. Cl.
CPC ............ *C07K 16/40* (2013.01); *C07K 2317/11* (2013.01); *C07K 2317/23* (2013.01); *C07K 2316/96* (2013.01); *A61K 2039/505* (2013.01)
USPC .................... 424/146.1; 424/130.1; 424/139.1

(58) Field of Classification Search
None
See application file for complete search history.

(56) References Cited

U.S. PATENT DOCUMENTS

| 5,080,895 A | 1/1992 | Tokoro |
| 5,980,881 A | 11/1999 | Mitsuka et al. |
| 5,985,938 A | 11/1999 | Holmes-Farley et al. |
| 5,989,584 A | 11/1999 | Cook et al. |
| 6,180,094 B1 | 1/2001 | Sasaki et al. |
| 6,213,930 B1 | 4/2001 | Cook |
| 6,423,754 B1 | 7/2002 | Holmes-Farley et al. |
| 2002/0156266 A1 | 10/2002 | Cannon et al. |
| 2004/0087522 A1 | 5/2004 | Marquardt et al. |

FOREIGN PATENT DOCUMENTS

| WO | 9505184 | 2/1995 |
| WO | 9519373 A1 | 7/1995 |
| WO | 0203788 A2 | 1/2002 |
| WO | 2008051980 A2 | 5/2008 |
| WO | 2008067084 A2 | 6/2008 |

OTHER PUBLICATIONS

Uribarri et al. "Hidden sources of phosphorus in the typical American diet: does it matter in nephrology?" Semin Dial. 16(3), 1868, 2003.*
Goldberg et al. "Effect of RenaGel, a non-absorbed, calcium- and aluminium-free phosphate binder, on serum phosphorus, calcium, and intact parathyroid hormone in end-stage renal disease patients" Nephrol Dial Transplant, 1998, 13, 2303-2310.*
Notice of Rejection for Japanese Application No. 2009-534818 dated Aug. 14, 2012; 4 pages.
Tenenhouse et al., "Phosphate transport: Molecular basis, regulation and pathophysiology," Journal of Steriod Biochemistry and Molecular Biolody, Mar. 2007, vol. 103, No. 3-5, p. 572-577.
Lau K., Phosphate Disorders. Saunders; 1986:398-470.
Delmez, et al., "Hyperphosphatemia: Its consequences and treatment in patients with chronic renal disease," AM J Kidney Dis, 1992, 19:303-317.
Cross et al., Miner Electrolyte Metab 1990, 16:115-124.
Walton J et al., Clin Sci 1979, 56:407-412.
Hu et al., Miner Electrolyte Metab, 1997, 23:7-12.
Peters et al., Res Exp Med (Berl), 1988, 188:139-149.
Eto et al. Drug Metab Pharmacokinet, 2006, 21:217-221.
Knox F et al., Am. J. Physiol. 1977, 233:F261-F268.
Albaaj F & Hutchinson A, Drugs 2003, 63:577-596.
Block G et al., J. Am. Soc. Nephrol. 2004, 15:2208-2218.
Block G & Port F, Am. J. Kidney Dis. 2000, 35:1226-1237.
Hilfiker H., et al., Proc Natl Acad Sci USA. 1998, 95:14564-14569.
Pileggi et al., Arch. Biochem. Biophys. 1995, 58:194-204.
Nakano et al., Arch Histol Cytol 2001, 64:483-491.
Atuma et al., Am J Physiol Gastrointest Liver Physiol 2001, 280:922.
M. Mantle and Al Allen, 1989, Gastrointestinal mucus, pp. 202-229 in Gastrointestinal Secretions, J.S. Davidson, ed., Butterworth and Co., Great Britain.
Kostelny, et al., "Formation of a bispecific antibody by the use of leucine zippers," J. Immunol. 1992, 148:1547-1553.
Pack and Pluckthun, "Miniantibodies: use of amphipathic helixes to produce functional, flexibly linked dimeric FV fragments with high avidity in *Escherichia coli*," Biochemistry 1992, 31:1579-1584.
Zhu, et al., "Remodeling Domain Interfaces to Enhance Heterodimer Formation," Protein Sci 1997, 6:781-788.
Hu, et al., "Minibody: A Novel Engineered Anti-Carcinoembryonic Antigen Antibody Fragment (Single-Chain Fv-CH3) Which Exhibits Rapid, High-Level Targeting of Xenografts," Cancer Res. 1996, 56:3055-3061.
Adams et al., "Highly Specific in Vivo Tumor Targeting by Monovalent and Divalent Forms of 741F8 Anti-c-erbB-2 Single-Chain Fv," Cancer Res 1993, 53:4026-4034.
McCartney, et al., "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides," Protein Eng. 1995, 8:301-314.

(Continued)

*Primary Examiner* — Daniel E Kolker
*Assistant Examiner* — James Rogers
(74) *Attorney, Agent, or Firm* — Armstrong Teasdale LLP

(57) ABSTRACT

It is disclosed here a method for reducing phosphate absorption in a human or non-human animal subject wherein the subject consumes a diet containing phytic acid or phytate and either has or is at risk of developing hyperphosphatemia. The method includes the step of administering orally to the subject an anti-intestinal alkaline phosphatase antibody in an amount effective to reduce or maintain the serum phosphate concentration in the subject.

17 Claims, 6 Drawing Sheets

(56) References Cited

OTHER PUBLICATIONS

Bouillon et al., Endocrine Reviews 1995, 16:200-257.
Altschul et al., (Nucleic Acids Res. 25, 3389-3402, 1997).
Polson, A., M.B. von Wechmar and M.H. van Regenmortel, "Isolation of Viral IgY Antibodies from Yolks of Immunized Hens," Immunological Communications 9:475-493 (1980).
Camenisch C et al., FASEB J. 1999, 13:81-88.
Akita E & Nakai S, J. Immunol. Methods 1993, 160:207-214.
Yokazawa et al. Nephron 1986, 44:230-234.
Katsumata et al. Kid Intl 2003, 64:441-450.
Levi R et al. J Am Soc Nephrol 2006, 17:107-112.
Cozzolino M et al., Kidney Int. 2003, 64:1653-61.
International Search Report and Written Opinion regarding PCT/US2007/082244, dated May 7, 2008.
Yudd, et al.: "Current medical management of secondary hyperparathyroidism" American Journal of Medical Sciences, vol. 320, No. 2, Aug. 2000, pp. 100-106.
Sogabe, et al: "Enhancement by lactose if intestinal alkaline phosphatase expression in rats" Bone (New York), vol. 35, No. 1, Jul. 2004, pp. 249-255.
Roubaty, et al. "Relation between intestinal alkaline phosphatase activity and brush border membrane transport of inorganic phosphate, D-glucose, and D-glucose-6-phosphate" Pfluegers Archiv: European Journal of Physiology, vol. 412, No. 5, Oct. 1988, pp. 482-490.
Hirano, et al. "Role of Alkaline Phosphatase in Phosphate Uptake Into Brush Border Membrane Vesicles From Human Intestinal Mucosa" Journal of Biochemistry, vol. 97, No. 5, 1985, pp. 1461-1466.
Kovacs-Nolan, et al. "Microencapsulation for the gastric passage and controlled intestinal release of immunoglobulin Y" Journal of Immunological Methods, vol. 296, No. 1-2, Jan. 2005, pp. 199-209.
Schlemmer, et al. "Degradation of phytate in the gut of pigs—pathway of gastro-intestinal inositol phosphate hydrolysis and enzymes involved" Archiv Fuer Tierernaehrung—Archives of Animal Nutrition, vol. 55, No. 4, 2001, pp. 255-280.
Biehl, et al. "1-alpha-Hydroxycholecalciferol does not increase the specific activity of intestinal phytase but does improve phosphorus utilization in both cecectomized and sham-operated chicks fed cholecalciferol-adequate diets" Journal of Nutrition, vol. 127, No. 10, 1997, pp. 2054-2059.
Schade, et al., "Chicken Egg Yolk Antibodies (IGY-Technology): A Review of Progress in Production and Use in Research and Human and Veterinary Medicine," Alternatives to Laboratory Animals, Apr. 1, 2005, vol. 33, No. 2, p. 129-154.
Katai, et al., "Regulation of intestinal Na+-dependent phosphate co-transporters by a low-phosphate diet and 1,25-dihydroxyvitamin D3," Biochemical Journal, Nov. 1, 1999, vol. 343, No. 3, p. 705-712.
Xu, et al., "Age-dependent regulation of rat intestinal type IIb sodium-phosphate cotransporter by 1,25-(OH)2 vitamin D3," American Journal of Physiology—Cell Physiology, 2005, vol. 282, No. 3, p. C487-C493.
International Search Report from PCT/US2007/082247, dated Apr. 23, 2008.
Fertel, et al., "Formation of Antibodies to Prostaglandins in the Yolk of Chicken Eggs," Biochemical and Biophysical Research Communications, vol. 102, No. 3, Oct. 15, 1981, p. 1028-1033.
Homann, et al., "Sodium-phosphate cotransporter in human salivary glands: Molecular evidence for the involvement of NPT2b in acinar phosphate secretion and ductal phosphate reabsorption," Archives of Oral Biology, Sep. 2005, vol. 50, No. 9, p. 759-768.
Karim-Jimenez, et al., "Molecular determinants for apical expression of teh renal type IIa Na<+>/Pi-cotransporter," Pflugers Archiv European Journal of Physiology, 2001, vol. 442, No. 5, p. 782-790.
Prie, et al., "Recent findings in phosphate homeostasis," Current Opinion in Nephrology and Hypertension, Jul. 2005, vol. 14, No. 4, p. 318-324.
Stollar, et al., "Cross-reactions of nucleic acids with monoclonal antibodies to phosphatidylinositol phosphate and cholesterol," Molecular Immunology, Jan. 1, 1989, vol. 26, No. 1, p. 73-79.
Horie, et al., "Suppressive effect of functional drinking yogurt containing specific egg yolk immunoglobulin on Helicobacter pylori in humans," Journal of Dairy Science, Dec. 2004, vol. 87, No. 12, p. 4073-4079.
Levi, et al., "Renal phosphate-wasting disorders," Advances in Chronic Kidney Disease, Apr. 2006, vol. 13, No. 2, p. 155-165.
International Search Report from PCT/US2007/082236, dated Jun. 5, 2008.
First Examiner's Report of the Australian Patent Office for Australian Patent Application No. 2007309026, dated Apr. 18, 2012.
Uribarri et al., "Hidden Sources for Phosphorus in the Typical American Diet: Does it Matter in Nephrology?" Sminars in Dialysis, 2003, vol. 16, No. 3, pp. 186-188.
Biehl et al., "1 alpha-Hydroxycholecalciferol Does Not Increase the Specific Activity of Intestinal Phytase but Does Improve Phosphorus Utilization in Both Cecectomized and Sham-Operated Chicks Fed Cholecalciferol-Adequate Diets", J. Nutr, 1997, vol. 127, No. 10, pp. 2054-2059.
First Office Action for Chinese Application No. 200780048139.1 dated Nov. 3, 2011.
Second Office Action for Chinese Application No. 200780048139.1 dated Jul. 31, 2012.
EP Office Action for Application No. 07 844 535.0-1412 dated May 14, 2013; 5 pages.
Australian Office Action for Patent Application No. 2007309026 dated Mar. 27, 2013; 3 pages.

* cited by examiner

```
                         SEQUENCE LISTING

<160> NUMBER OF SEQ ID NOS: 21

<210> SEQ ID NO 1
<211> LENGTH: 528
<212> TYPE: PRT
<213> ORGANISM: Homo sapiens

<400> SEQUENCE: 1

Met Gln Gly Pro Trp Val Leu Leu Leu Gly Leu Arg Leu Gln Leu
1               5                   10                  15

Ser Leu Gly Val Ile Pro Ala Glu Glu Glu Asn Pro Ala Phe Trp Asn
                20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
```

```
            100                 105                 110
Ala Thr Ala Thr Ala Tyr Leu Cys Gly Val Lys Ala Asn Phe Gln Thr
            115                 120                 125

Ile Gly Leu Ser Ala Ala Arg Phe Asn Gln Cys Asn Thr Thr Arg
    130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
                180                 185                 190

Met Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile Leu Arg Asp Pro Thr Leu Asp
    290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Val Thr Glu Ala Val Met
                340                 345                 350

Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
                420                 425                 430

Ser Gly Ser Pro Asp Tyr Gln Gln Ala Ala Val Pro Leu Ser Ser
                435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Leu Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
        515                 520                 525
```

```
<210> SEQ ID NO 2
<211> LENGTH: 559
<212> TYPE: PRT
<213> ORGANISM: mouse

<400> SEQUENCE: 2

Met Gln Gly Pro Trp Val Leu Leu Leu Gly Leu Arg Leu Gln Leu
1               5                   10                  15

Ser Leu Ser Val Ile Pro Val Glu Glu Asn Pro Ala Phe Trp Asn
                20                  25                  30

Lys Lys Ala Ala Glu Ala Leu Asp Ala Ala Lys Lys Leu Gln Pro Ile
            35                  40                  45

Gln Thr Ser Ala Lys Asn Leu Ile Ile Phe Leu Gly Asp Gly Met Gly
        50                  55                  60

Val Pro Thr Val Thr Ala Thr Arg Ile Leu Lys Gly Gln Leu Glu Gly
65                  70                  75                  80

His Leu Gly Pro Glu Thr Pro Leu Ala Met Asp Arg Phe Pro Tyr Met
                85                  90                  95

Ala Leu Ser Lys Thr Tyr Ser Val Asp Arg Gln Val Pro Asp Ser Ala
            100                 105                 110

Ser Thr Ala Thr Ala Tyr Leu Cys Gly Val Lys Thr Asn Tyr Lys Thr
        115                 120                 125

Ile Gly Leu Ser Ala Ala Arg Phe Asp Gln Cys Asn Thr Thr Phe
        130                 135                 140

Gly Asn Glu Val Phe Ser Val Met Tyr Arg Ala Lys Lys Ala Gly Lys
145                 150                 155                 160

Ser Val Gly Val Val Thr Thr Thr Arg Val Gln His Ala Ser Pro Ser
                165                 170                 175

Gly Thr Tyr Val His Thr Val Asn Arg Asn Trp Tyr Gly Asp Ala Asp
            180                 185                 190

Met Pro Ala Ser Ala Leu Arg Glu Gly Cys Lys Asp Ile Ala Thr Gln
        195                 200                 205

Leu Ile Ser Asn Met Asp Ile Asn Val Ile Leu Gly Gly Gly Arg Lys
210                 215                 220

Tyr Met Phe Pro Ala Gly Thr Pro Asp Pro Glu Tyr Pro Asn Asp Ala
225                 230                 235                 240

Asn Glu Thr Gly Thr Arg Leu Asp Gly Arg Asn Leu Val Gln Glu Trp
                245                 250                 255

Leu Ser Lys His Gln Gly Ser Gln Tyr Val Trp Asn Arg Glu Gln Leu
            260                 265                 270

Ile Gln Lys Ala Gln Asp Pro Ser Val Thr Tyr Leu Met Gly Leu Phe
        275                 280                 285

Glu Pro Val Asp Thr Lys Phe Asp Ile Gln Arg Asp Pro Leu Met Asp
290                 295                 300

Pro Ser Leu Lys Asp Met Thr Gly Thr Ala Val Lys Val Leu Ser Arg
305                 310                 315                 320

Asn Pro Lys Gly Phe Tyr Leu Phe Val Glu Gly Gly Arg Ile Asp Arg
                325                 330                 335

Gly His His Leu Gly Thr Ala Tyr Leu Ala Leu Thr Glu Ala Val Met
            340                 345                 350

Phe Asp Leu Ala Ile Glu Arg Ala Ser Gln Leu Thr Ser Glu Arg Asp
        355                 360                 365

Thr Leu Thr Ile Val Thr Ala Asp His Ser His Val Phe Ser Phe Gly
```

```
            370                 375                 380
Gly Tyr Thr Leu Arg Gly Thr Ser Ile Phe Gly Leu Ala Pro Leu Asn
385                 390                 395                 400

Ala Leu Asp Gly Lys Pro Tyr Thr Ser Ile Leu Tyr Gly Asn Gly Pro
                405                 410                 415

Gly Tyr Val Gly Thr Gly Glu Arg Pro Asn Val Thr Ala Ala Glu Ser
            420                 425                 430

Ser Gly Ser Ser Tyr Arg Arg Gln Ala Ala Val Pro Val Lys Ser Glu
        435                 440                 445

Thr His Gly Gly Glu Asp Val Ala Ile Phe Ala Arg Gly Pro Gln Ala
    450                 455                 460

His Leu Val His Gly Val Gln Glu Gln Asn Tyr Ile Ala His Val Met
465                 470                 475                 480

Ala Ser Ala Gly Cys Leu Glu Pro Tyr Thr Asp Cys Gly Leu Ala Pro
                485                 490                 495

Pro Ala Asp Glu Ser Gln Thr Thr Thr Thr Thr Arg Gln Thr Thr Ile
            500                 505                 510

Thr Thr Thr Thr Thr Thr Thr Thr Thr Thr Thr Thr Pro Val His Asn
        515                 520                 525

Ser Ala Arg Ser Leu Gly Pro Ala Thr Ala Pro Leu Ala Leu Ala Leu
    530                 535                 540

Leu Ala Gly Met Leu Met Leu Leu Gly Ala Pro Ala Glu Ser
545                 550                 555

<210> SEQ ID NO 3
<211> LENGTH: 540
<212> TYPE: PRT
<213> ORGANISM: rat

<400> SEQUENCE: 3

Met Gln Gly Asp Trp Val Leu Leu Leu Leu Gly Leu Arg Ile His
1               5                   10                  15

Leu Ser Phe Gly Val Ile Pro Val Glu Glu Asn Pro Val Phe Trp
                20                  25                  30

Asn Gln Lys Ala Lys Glu Ala Leu Asp Val Ala Lys Lys Leu Gln Pro
            35                  40                  45

Ile Gln Thr Ser Ala Lys Asn Leu Ile Leu Phe Leu Gly Asp Gly Met
50                  55                  60

Gly Val Pro Thr Val Thr Ala Thr Arg Ile Leu Lys Gly Gln Leu Gly
65                  70                  75                  80

Gly His Leu Gly Pro Glu Thr Pro Leu Ala Met Asp His Phe Pro Phe
                85                  90                  95

Thr Ala Leu Ser Lys Thr Tyr Asn Val Asp Arg Gln Val Pro Asp Ser
                100                 105                 110

Ala Gly Thr Ala Thr Ala Tyr Leu Cys Gly Val Lys Ala Asn Tyr Lys
            115                 120                 125

Thr Ile Gly Val Ser Ala Ala Arg Phe Asn Gln Cys Asn Ser Thr
            130                 135                 140

Phe Gly Asn Glu Val Phe Ser Val Met His Arg Ala Lys Lys Ala Gly
145                 150                 155                 160

Lys Ser Val Gly Val Val Thr Thr Thr Arg Val Gln His Ala Ser Pro
                165                 170                 175

Ala Gly Thr Tyr Ala His Thr Val Asn Arg Asp Trp Tyr Ser Asp Ala
            180                 185                 190
```

```
Asp Met Pro Ser Ser Ala Leu Gln Glu Gly Cys Lys Asp Ile Ala Thr
            195                 200                 205

Gln Leu Ile Ser Asn Met Asp Ile Asp Val Ile Leu Gly Gly Gly Arg
        210                 215                 220

Lys Ser Met Phe Pro Lys Gly Thr Pro Asp Pro Glu Tyr Pro Gly Asp
225                 230                 235                 240

Ser Asp Gln Ser Gly Val Arg Leu Asp Ser Arg Asn Leu Val Glu Glu
                245                 250                 255

Trp Leu Ala Lys Tyr Gln Gly Thr Arg Tyr Val Trp Asn Arg Glu Gln
            260                 265                 270

Leu Met Arg Ala Ser Gln Asp Pro Ala Val Thr Arg Leu Met Gly Leu
        275                 280                 285

Phe Glu Pro Thr Glu Met Lys Tyr Asp Val Asn Arg Asn Ala Ser Ala
    290                 295                 300

Asp Pro Ser Leu Ala Glu Met Thr Glu Val Ala Val Arg Leu Leu Ser
305                 310                 315                 320

Arg Asn Pro Gln Gly Phe Tyr Leu Phe Val Glu Gly Gly Arg Ile Asp
                325                 330                 335

Gln Gly His His Ala Gly Thr Ala Tyr Leu Ala Leu Thr Glu Ala Ala
            340                 345                 350

Met Phe Asp Ser Ala Ile Glu Lys Ala Ser Gln Leu Thr Asn Glu Lys
        355                 360                 365

Asp Thr Leu Thr Leu Ile Thr Ala Asp His Ser His Val Phe Ala Phe
    370                 375                 380

Gly Gly Tyr Thr Leu Arg Gly Thr Ser Ile Phe Gly Leu Ala Pro Leu
385                 390                 395                 400

Asn Ala Gln Asp Gly Lys Ser Tyr Thr Ser Ile Leu Tyr Gly Asn Gly
                405                 410                 415

Pro Gly Tyr Val Leu Asn Ser Gly Asn Arg Pro Asn Val Thr Asp Ala
            420                 425                 430

Glu Ser Gly Asp Val Asn Tyr Lys Gln Gln Ala Ala Val Pro Leu Ser
        435                 440                 445

Ser Glu Thr His Gly Gly Glu Asp Val Ala Ile Phe Ala Arg Gly Pro
    450                 455                 460

Gln Ala His Leu Val His Gly Val Gln Glu Gln Asn Tyr Ile Ala His
465                 470                 475                 480

Val Met Ala Phe Ala Gly Cys Leu Glu Pro Tyr Thr Asp Cys Gly Leu
                485                 490                 495

Ala Pro Pro Ala Asp Glu Asn Arg Pro Thr Thr Pro Val Gln Asn Ser
            500                 505                 510

Ala Ile Thr Met Asn Asn Val Leu Leu Ser Leu Gln Leu Leu Val Ser
        515                 520                 525

Met Leu Leu Leu Val Gly Thr Ala Leu Val Val Ser
    530                 535                 540

<210> SEQ ID NO 4
<211> LENGTH: 562
<212> TYPE: PRT
<213> ORGANISM: rat

<400> SEQUENCE: 4

Met Gln Gly Ala Trp Val Leu Leu Leu Gly Phe Arg Leu Gln Leu
1               5                   10                  15

Ser Leu Ser Val Ile Pro Val Glu Glu Glu Asn Pro Ala Phe Trp Asn
            20                  25                  30
```

-continued

```
Gln Lys Ala Ala Asp Ala Leu Asn Val Ala Lys Lys Leu Gln Pro Ile
         35                  40                  45

Gln Thr Ser Ala Lys Asn Leu Ile Ile Phe Leu Gly Asp Gly Met Gly
 50                  55                  60

Val Pro Thr Val Thr Ala Thr Arg Ile Leu Lys Gly Gln Leu Glu Gly
 65                  70                  75                  80

Asn Leu Gly Pro Glu Thr Pro Leu Ala Met Asp His Phe Pro Tyr Met
                 85                  90                  95

Ala Leu Ser Lys Thr Tyr Ser Val Asp Arg Gln Val Pro Asp Ser Ala
                100                 105                 110

Ser Thr Ala Thr Ala Tyr Leu Cys Gly Val Lys Thr Asn Tyr Lys Thr
                115                 120                 125

Ile Gly Val Ser Ala Ala Ala Arg Phe Asp Gln Cys Asn Thr Thr Phe
    130                 135                 140

Gly Asn Glu Val Leu Ser Val Met Tyr Arg Ala Lys Lys Ala Gly Lys
145                 150                 155                 160

Ser Val Gly Val Val Thr Thr Thr Arg Val Gln His Ala Ser Pro Ala
                165                 170                 175

Gly Thr Tyr Val His Thr Val Asn Arg Asn Trp Tyr Gly Asp Ala Asp
                180                 185                 190

Met Pro Ala Ser Ala Leu Gln Glu Gly Cys Lys Asp Ile Ala Thr Gln
    195                 200                 205

Leu Ile Ser Asn Met Asp Ile Asn Val Ile Leu Gly Gly Gly Arg Lys
    210                 215                 220

Tyr Met Phe Pro Ala Gly Thr Pro Asp Pro Glu Tyr Pro Asn Asp Val
225                 230                 235                 240

Asn Glu Thr Gly Thr Arg Leu Asp Gly Lys Asn Leu Val Gln Glu Trp
                245                 250                 255

Leu Ser Lys His Gln Gly Ser Gln Tyr Val Trp Asn Arg Gln Glu Leu
                260                 265                 270

Ile Gln Lys Ser Leu Asp Pro Ser Val Thr Tyr Leu Met Gly Leu Phe
    275                 280                 285

Glu Pro Val Asp Thr Lys Phe Glu Ile Gln Arg Asp Pro Leu Met Asp
    290                 295                 300

Pro Ser Leu Lys Asp Met Thr Glu Ala Ala Leu His Val Leu Ser Arg
305                 310                 315                 320

Asn Pro Lys Gly Phe Tyr Leu Phe Val Glu Gly Gly Arg Ile Asp Arg
                325                 330                 335

Gly His His Leu Gly Thr Ala Tyr Leu Ala Leu Thr Glu Ala Val Met
                340                 345                 350

Leu Asp Ser Ala Ile Glu Arg Ala Ser Gln Leu Thr Ser Glu Gln Asp
    355                 360                 365

Thr Leu Thr Ile Val Thr Ala Asp His Ser His Val Phe Ser Phe Gly
    370                 375                 380

Gly Tyr Thr Leu Arg Gly Thr Ser Ile Phe Gly Leu Ala Pro Leu Asn
385                 390                 395                 400

Ala Leu Asp Gly Lys Pro Tyr Thr Ser Ile Leu Tyr Gly Asn Gly Pro
                405                 410                 415

Gly Tyr Val Gly Thr Gly Glu Arg Pro Asn Val Thr Asp Ala Glu Ser
                420                 425                 430

His Asp Pro Ser Tyr Gln Gln Ala Ala Val Pro Val Lys Ser Glu
    435                 440                 445
```

```
Thr His Gly Gly Glu Asp Val Ala Ile Phe Ala Arg Gly Pro Gln Ala
            450                 455                 460

His Leu Leu His Gly Val Gln Glu Gln Asn Tyr Ile Ala His Val Met
465                 470                 475                 480

Ala Phe Ala Gly Cys Leu Glu Pro Tyr Thr Asp Cys Gly Leu Ala Pro
                485                 490                 495

Pro Ala Asp Glu Asn Arg Pro Thr Thr Pro Val Gln Asn Ser Thr Thr
            500                 505                 510

Thr Thr Thr Thr Thr Thr Thr Thr Thr Thr Thr Thr Thr Thr Thr Arg
            515                 520                 525

Val Gln Asn Ser Ala Ser Ser Leu Gly Pro Ala Thr Gly Pro Leu Ala
            530                 535                 540

Leu Ala Leu Leu Ala Lys Ala Leu Met Leu Leu Leu Gly Ala Pro Ala
545                 550                 555                 560

Asp Phe

<210> SEQ ID NO 5
<211> LENGTH: 8
<212> TYPE: PRT
<213> ORGANISM: Artificial
<220> FEATURE:
<223> OTHER INFORMATION: synthetic peptide

<400> SEQUENCE: 5

Gly Pro Glu Thr Pro Leu Ala Met
1               5

<210> SEQ ID NO 6
<211> LENGTH: 8
<212> TYPE: PRT
<213> ORGANISM: Artificial
<220> FEATURE:
<223> OTHER INFORMATION: synthetic peptide

<400> SEQUENCE: 6

Lys Thr Tyr Asn Val Asp Arg Gln
1               5

<210> SEQ ID NO 7
<211> LENGTH: 8
<212> TYPE: PRT
<213> ORGANISM: Artificial
<220> FEATURE:
<223> OTHER INFORMATION: synthetic peptide

<400> SEQUENCE: 7

Lys Ala Asn Phe Gln Thr Ile Gly
1               5

<210> SEQ ID NO 8
<211> LENGTH: 8
<212> TYPE: PRT
<213> ORGANISM: Artificial
<220> FEATURE:
<223> OTHER INFORMATION: synthetic peptide

<400> SEQUENCE: 8

Lys Gln Ala Gly Lys Ser Val Gly
1               5

<210> SEQ ID NO 9
<211> LENGTH: 8
<212> TYPE: PRT
```

```
<213> ORGANISM: Artificial
<220> FEATURE:
<223> OTHER INFORMATION: synthetic peptide

<400> SEQUENCE: 9

His Thr Val Asn Arg Asn Trp Tyr
1               5

<210> SEQ ID NO 10
<211> LENGTH: 8
<212> TYPE: PRT
<213> ORGANISM: Artificial
<220> FEATURE:
<223> OTHER INFORMATION: synthetic peptide

<400> SEQUENCE: 10

Met Phe Pro Met Gly Thr Pro Asp
1               5

<210> SEQ ID NO 11
<211> LENGTH: 8
<212> TYPE: PRT
<213> ORGANISM: Artificial
<220> FEATURE:
<223> OTHER INFORMATION: synthetic peptide

<400> SEQUENCE: 11

Glu Ala Ala Leu Arg Leu Leu Ser
1               5

<210> SEQ ID NO 12
<211> LENGTH: 8
<212> TYPE: PRT
<213> ORGANISM: Artificial
<220> FEATURE:
<223> OTHER INFORMATION: synthetic peptide

<400> SEQUENCE: 12

Gly Arg Ile Asp His Gly His His
1               5

<210> SEQ ID NO 13
<211> LENGTH: 8
<212> TYPE: PRT
<213> ORGANISM: Artificial
<220> FEATURE:
<223> OTHER INFORMATION: synthetic peptide

<400> SEQUENCE: 13

Phe Gly Gly Tyr Thr Leu Arg Gly
1               5

<210> SEQ ID NO 14
<211> LENGTH: 8
<212> TYPE: PRT
<213> ORGANISM: Artificial
<220> FEATURE:
<223> OTHER INFORMATION: synthetic peptide

<400> SEQUENCE: 14

Leu Ser Ser Glu Thr His Gly Gly
1               5

<210> SEQ ID NO 15
<211> LENGTH: 8
<212> TYPE: PRT
<213> ORGANISM: Artificial
```

```
<220> FEATURE:
<223> OTHER INFORMATION: synthetic peptide

<400> SEQUENCE: 15

Gln Ala Ala Glu Ala Leu Asp Ala
1               5

<210> SEQ ID NO 16
<211> LENGTH: 8
<212> TYPE: PRT
<213> ORGANISM: Artificial
<220> FEATURE:
<223> OTHER INFORMATION: synthetic peptide

<400> SEQUENCE: 16

Arg Ile Leu Lys Gly Gln Lys Asn
1               5

<210> SEQ ID NO 17
<211> LENGTH: 8
<212> TYPE: PRT
<213> ORGANISM: Artificial
<220> FEATURE:
<223> OTHER INFORMATION: synthetic peptide

<400> SEQUENCE: 17

Gln His Ala Ser Pro Ala Gly Thr
1               5

<210> SEQ ID NO 18
<211> LENGTH: 8
<212> TYPE: PRT
<213> ORGANISM: Artificial
<220> FEATURE:
<223> OTHER INFORMATION: synthetic peptide

<400> SEQUENCE: 18

Asp Ala Asp Met Pro Ala Ser Ala
1               5

<210> SEQ ID NO 19
<211> LENGTH: 8
<212> TYPE: PRT
<213> ORGANISM: Artificial
<220> FEATURE:
<223> OTHER INFORMATION: synthetic peptide

<400> SEQUENCE: 19

His Gln Gly Ala Trp Tyr Val Trp
1               5

<210> SEQ ID NO 20
<211> LENGTH: 8
<212> TYPE: PRT
<213> ORGANISM: Artificial
<220> FEATURE:
<223> OTHER INFORMATION: synthetic peptide

<400> SEQUENCE: 20

Glu Leu Met Gln Ala Ser Leu Asp
1               5

<210> SEQ ID NO 21
<211> LENGTH: 8
<212> TYPE: PRT
<213> ORGANISM: Artificial
<220> FEATURE:
```

```
<223> OTHER INFORMATION: synthetic peptide

<400> SEQUENCE: 21

Leu Thr Ser Glu Glu Asp Thr Leu
1               5
```

METHODS OF REDUCING PHOSPHATE ABSORPTION

CROSS-REFERENCE TO RELATED APPLICATIONS

This application is a U.S. National Phase patent application of International Application Serial Number PCT/US2007/082244, filed on Oct. 23, 2007, which is herein incorporated by reference in its entirety, and which claims the benefit of U.S. provisional application Ser. No. 60/854,550, filed on Oct. 26, 2006, which is herein incorporated by reference in its entirety.

REFERENCE TO A SEQUENCE LISTING

This application includes a Sequence Listing. A paper copy and a computer readable copy of the Sequence Listing in a .txt file are being submitted concurrently herewith. The information contained in the Sequence Listing is herein incorporated by reference in its entirety.

STATEMENT REGARDING FEDERALLY SPONSORED RESEARCH OR DEVELOPMENT

Not applicable.

BACKGROUND OF THE INVENTION

Phosphorus is an essential element in human nutrition and plays essential structural and functional roles in the biochemistry, cellular integrity, and physiological processes of the body. In foods comprising animal or vegetable matter, phosphorus can be found as inorganic phosphate (Pi) (e.g., in its pentavalent form in combination with oxygen as phosphate ($PO_4^{3-}$)), which can be readily absorbed from the gastrointestinal tract. Also, phosphate can be found as a constituent of bio-macromolecules such as proteins, nucleic acids, lipids and sugars. Plant material can also be enriched in phytic acid ($C_6H_6[OPO(OH)_2]_6$), which is the principal storage form of phosphate (phytic phosphate) in many plant tissues (e.g., bran and seeds), accounting for 70% to 80% of phosphate in plants. Phytic acid or salts thereof (phytate) typically cannot be absorbed by monogastric animals and will pass out with the feces. Phytic acid/phytate can account for approximately 25% of an adult's daily dietary phosphate intake.

Phosphate is an essential component of bone mineral, as approximately 85% of phosphate in the adult body is in mineralized extracellular matrix, such as bone and teeth. Approximately 15% of phosphate is intracellular (e.g., in soft tissues) and about 0.1% is found in extracellular fluids (Tenenhouse et al., Vitamin D, 2nd edition, Elsevier, 2005). Cellular phosphate can also be found in the form of phospholipids which make up the structure of cellular membranes. Phosphate is also an essential structural component of nucleic acids such as DNA and RNA as well as nucleotides such as adenosine triphosphate (ATP) which is an important energy storage and transfer molecule and cyclic adenosine monophosphate which is an important cellular signaling molecule. Other physiological functions of intracellular phosphate include the following: (1) phosphorylation of a number of protein enzymes, hormones and cell signaling molecules for their activation; (2) maintaining normal acid-base balance as a physiological buffer; and (3) comprising the phosphate-containing molecule 2,3-diphosphoglycerate (2,3-DPG) in red blood cells. An average human contains about 700 to 1,000 grams of phosphorus (Lau K., Phosphate Disorders. Saunders; 1986:398-470), and consumes and excretes about one gram to about three grams of phosphorus per day in the form of $PO_4^{3-}$.

Humans maintain phosphate homeostasis by at least three routes—the gastrointestinal tract, kidneys, and bone. The gastrointestinal tract participates in phosphate homeostasis as an organ of phosphate absorption and excretion/resorption. Bone serves as a reservoir of phosphate which can be mobilized in response to various physiological signals. Gastrointestinal absorption of dietary phosphate is very efficient, with the principal sites of absorption being the duodenum and the jejunum (Delmez J A et al., Am J Kidney Dis, 1992, 19:303-317). A variable amount of dietary phosphate (10% to 80% of the ingested amount) is excreted in feces, depending on whether the diet is of plant origin (largely inaccessible phosphate) or animal tissue origin (largely digestible). Inorganic phosphate in food is absorbed in two ways, an active transcellular route via the brush border membrane and a passive paracellular route via tight junctions between cells (Cross et al., Miner Electrolyte Metab 1990, 16:115-124, and Walton J et al., Clin Sci 1979, 56:407-412). Some reports based on rat studies indicate that colonic phosphate transport is mediated mainly through the paracellular diffusive pathway (Hu et al., Miner Electrolyte Metab, 1997, 23:7-12; and Peters et al., Res Exp Med (Berl), 1988, 188:139-149). Other reports based on rat studies suggest that transcellular active transport is the dominant route in phosphate absorption across small intestine (Eto et al., Drug Metab Pharmacokinet, 2006, 21:217-221).

The kidney participates in phosphate homeostasis as an organ of phosphate filtration, reabsorption and excretion. The kidney is the main regulatory organ that maintains phosphate homeostasis. In healthy adult individuals, daily renal phosphate excretion equals the amount of daily gastrointestinal phosphate absorption. However, in states of phosphate depletion, the kidneys reduce urinary phosphate excretion to virtually zero (Knox F et al., Am. J. Physiol. 1977, 233:F261-F268). Renal phosphate reabsorption occurs mainly in the proximal tubule. The fractional urinary excretion of phosphate can vary between 0.1% to 20%, thus representing a powerful homeostatic mechanism. In severe renal failure, such as that resulting from chronic kidney disease, hyperphosphatemia occurs from inadequate renal phosphate clearance.

Primary regulatory factors of phosphate homeostasis are serum phosphate and parathyroid hormone (PTH). Increased serum phosphate levels enhance urinary excretion of phosphate. PTH decreases tubular phosphate reabsorption and increasing excretion of soluble phosphate into the urine. Other factors that affect phosphate homeostasis include, but are not limited to, age, diet (i.e. amount of phosphate ingested and/or chemical form of phosphate ingested), disease, pharmaceutical agents and diurnal variation.

Vitamin D, especially its active form 1,25-dihydroxyvitamin D (also called calcitriol), can also affect phosphate homeostasis by directly stimulating intestinal absorption of phosphate. In addition, vitamin D enhances bone resorption through mobilization of calcium and phosphate into the plasma (Albaaj F & Hutchison A, Drugs 2003, 63:577-596).

An example of abnormal phosphate homeostasis is hyperphosphatemia, which can occur by one or more of the following three mechanisms. The first mechanism is excessive phosphate absorption. The second mechanism is decreased phosphate excretion. The third mechanism is shifting phosphate from intracellular spaces to extracellular spaces. Severe hyperphosphatemia can cause paralysis, convulsions and cardiac arrest. Hyperphosphatemia occurs at serum phosphate concentrations above 5 mg/dl, which is associated with an increased risk of death (Block G et al., J. Am. Soc. Nephrol. 2004, 15:2208-2218). A normal physiological serum phosphate concentration is generally considered to be a serum phosphate concentration between about 2.4 mg/dl to about 4.5 mg/dl (Block G & Port F, Am. J. Kidney Dis. 2000, 35:1226-1237).

Patients with impaired kidney function can develop hyperphosphatemia as a result of decreased phosphate excretion by the kidney. Hyperphosphatemia ensues either when the vascular supply to the kidneys becomes reduced or when the glomeruli become damaged and cease filtering phosphate from the blood. As such, hyperphosphatemia is a predictable consequence of kidney disease and most kidney disease patients either have or will develop hyperphosphatemia. Examples of such kidney diseases include, but are not limited to, end stage renal disease, acute renal failure, chronic renal failure, polycystic kidney disease, chronic kidney disease, acute tubular necrosis (e.g., renal artery stenosis), infections that reduce kidney function (e.g., septicemia or kidney infection such as acute pyelonephritis), kidney transplantation rejection, and urinary tract obstruction.

Hyperphosphatemia associated with chronic kidney disease leads to severe pathophysiologies in calcium and phosphate homeostasis, especially if present over extended periods of time. Such pathophysiologies include, but are not limited to, hyperparathyroidism, bone disease (e.g., renal osteodystrophy) and calcification in joints, lungs, eyes and vasculature. Hyperphosphatemia in patients with chronic kidney disease is independently associated with mortality risk and the exact mechanism by which hyperphosphatemia increases mortality risk is unknown. For individuals who exhibit renal insufficiency, an elevation of serum phosphate within the normal range has been associated with progression of renal failure and increased risk of cardiovascular events. The National Kidney Foundation Kidney Disease Outcomes Quality Initiative Clinical Practice Guidelines for Bone Metabolism and Disease in Chronic Kidney Disease recommends maintenance of serum phosphate below 5.5 mg/dl, calcium-phosphate (Ca×P) product less than 55 mg$^2$/dl$^2$, and intact parathyroid hormone (iPTH) between 150 pg/ml and 300 pg/ml. Although the etiology is not fully demonstrated, high calcium-phosphate product has been held responsible for soft tissue calcification and cardiovascular disease. Cardiovascular disease is the cause of death in almost half of all dialysis patients.

Many kidney disease patients need to take an active form of vitamin D such as 1α, 25-dihydroxyvitamin D$_3$ for maintaining calcium homeostasis and/or for treating or preventing hypocalcemia and/or secondary hyperparathyroidism because these patients are deficient in active vitamin D. Vitamin D$_3$ is first metabolized to 25-hydroxyvitamin D$_3$ (also called calcidiol) in the liver and subsequently to 1α,25-dihydroxyvitamin D$_3$ in the kidney. 1α,25-dihydroxyvitamin D$_3$ is much more active than 25-hydroxyvitamin D$_3$. Kidneys with impaired function cannot convert 25-hydroxyvitamin D$_3$ to 1α,25-dihydroxyvitamin D$_3$. The low 1α,25-dihydroxyvitamin D$_3$ level stimulates the parathyroid gland to secret more PTH and parathyroid hyperplasia and secondary hyperparathyroidism ensue. Standard treatment of secondary hyperparathyroidism in individuals with chronic kidney disease includes active vitamin D or its analogs. Likewise, approximately 70% of individuals with end stage renal disease or failure receive some form of vitamin D. As discussed above, vitamin D stimulates intestinal absorption of phosphate. Therefore, kidney disease patients who take vitamin D such as 1α,25-dihydroxyvitamin D$_3$ are more susceptible to hyperphosphatemia and can also have their existing hyperphosphatemia exacerbated due to a combination of increased phosphate absorption with concomitant decreased phosphate excretion.

Therapeutic efforts to reduce serum phosphate levels include, but are not limited to, dialysis, reduction in dietary phosphate intake, administration of nicotinamide, and oral administration of insoluble phosphate binders. Examples of insoluble phosphate binders include, but are not limited to, aluminum compounds (e.g., Amphojel® aluminum hydroxide gel), calcium compounds (e.g., calcium carbonate, acetate such as PhosLo® calcium acetate tablets, citrate, alginate, and ketoacid salts), anion exchange polymers (e.g., amine functional polymers described in U.S. Pat. Nos. 5,985,938, 5,980,881, 6,180,094, 6,423,754, and PCT publication WO 95/05184, Dowex® anion-exchange resins in the chloride form, RenaGel®, and polymer bound guanidinium hydrochloride), inorganic compounds such as lanthanum carbonate tetrahydrate (Fosrenal™), ferric salts of citrate and acetate, and a lanthanum based porous ceramic material (RenaZorb™).

BRIEF SUMMARY OF THE INVENTION

In one aspect, the present invention relates to a method for reducing phosphate absorption in a human or non-human animal subject wherein the subject consumes a diet containing phytic acid or phytate and either has or is at risk of developing hyperphosphatemia. The method includes the step of administering orally to the subject an anti-intestinal alkaline phosphatase antibody in an amount effective to reduce or maintain the serum phosphate concentration in the subject. The method may further include the step of observing a decrease or stabilization of the serum phosphate concentration. For example, the serum phosphate concentrations before and after the antibody treatment can be measured and compared.

The method disclosed herein can be used to attenuate or prevent hyperphosphatemia. In some embodiments, the serum phosphate concentration is reduced to or maintained at a level of or lower than about 150%, 125%, 120%, 115%, 110%, or 105% of a maximum physiological serum phosphate concentration in the accepted normal range. In some embodiments, the serum phosphate concentration is reduced to or maintained at a level within the normal range. For a human subject, the maximum high-normal serum phosphate concentration is 5.0 mg/dl. In a preferred embodiment, the serum phosphate concentration is reduced to or maintained at 5.5 mg/dl or lower or 5.0 mg/dl or lower in a human subject.

In some embodiments, the subject (e.g., a human subject) has a kidney disease, receives a vitamin D compound (e.g., 1α,25-dihydroxyvitamin D$_3$), or both wherein the vitamin D compound renders phytic phosphate in the diet available for absorption. In some embodiments, the subject is a human kidney disease patient who takes a vitamin D compound (e.g., 1α,25-dihydroxyvitamin D$_3$) and has a serum phosphate level above 5.0 mg/dl or 5.5 mg/dl. Examples of kidney diseases include end stage renal disease, acute renal failure, polycystic kidney disease, chronic kidney disease, acute tubular necrosis, infections that reduce kidney function (e.g., septicemia or kidney infection such as acute pyelonephritis), kidney transplantation rejection, or urinary tract obstruction.

In some embodiments, the antibody employed in the method is an IgY antibody. In some embodiments, the antibody is derived from an egg (e.g., egg yolk), and especially from an avian egg such as a chicken egg.

In some embodiments, the antibody is an antibody that binds to an epitope within amino acids 72-79, amino acids 83-90, amino acids 123-130, amino acids 181-188, amino acids 226-233, amino acids 260-267, amino acids 271-278, amino acids 312-319, amino acids 363-370, amino acids 383-390, or amino acids 446-453 of the human intestinal alkaline phosphatase defined by SEQ ID NO:1

In some embodiments, the anti-intestinal alkaline phosphatase antibody is administered concomitantly with a phosphate binder. In some embodiments, the anti-intestinal alkaline phosphatase antibody is administered with food or close in time (i.e. within about one hour before or after) to the consumption of a food having dietary phosphate such as phytic phosphate.

DETAILED DESCRIPTION OF THE INVENTION

Figure 1:
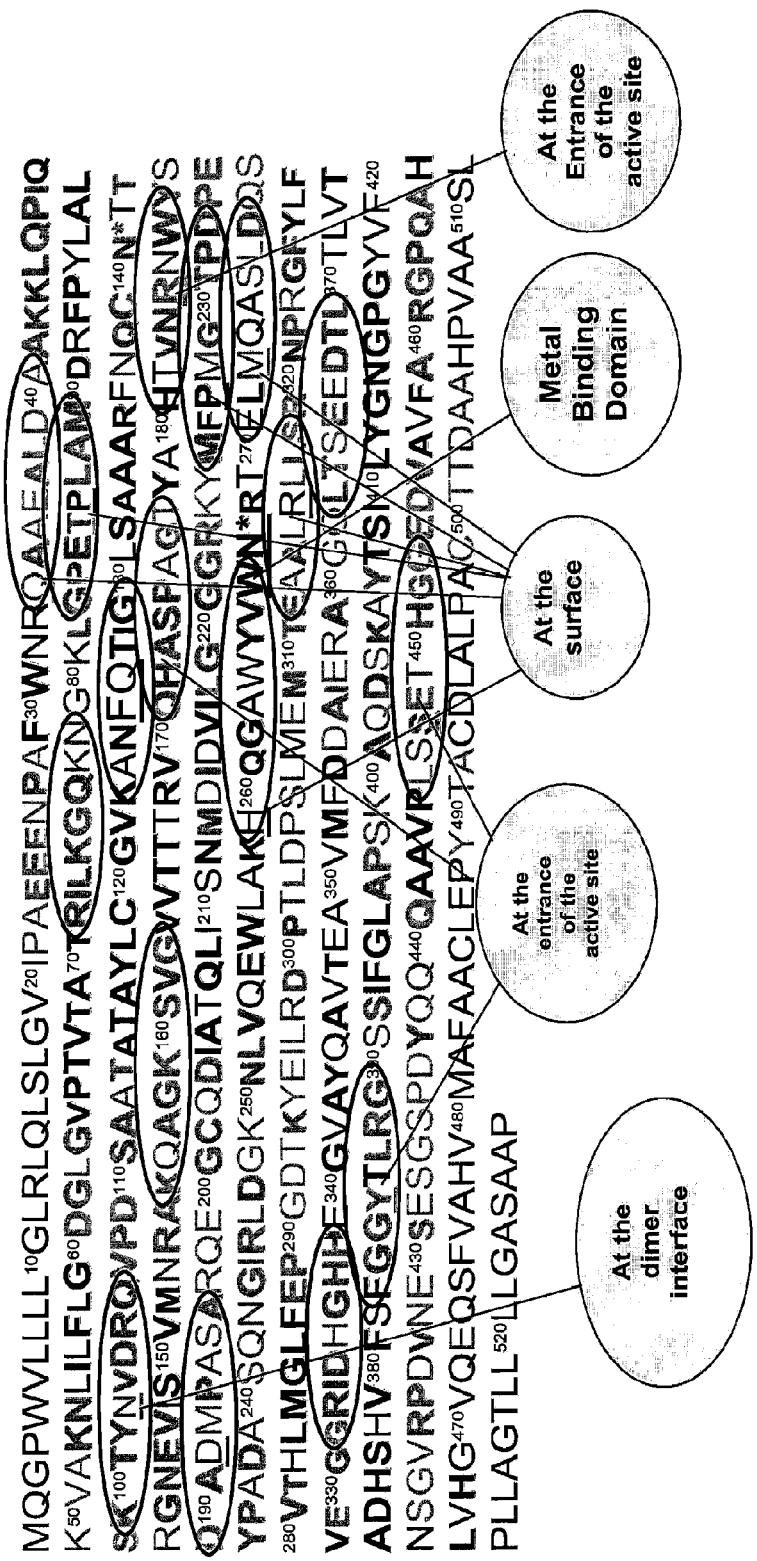
FIG. 1 shows the amino acid sequence of human intestinal alkaline phosphatase (SEQ ID NO:1) and the fragments (circled peptides) used to generate antibodies. The shadowed amino acids indicate those conserved among human, mouse, rat, dog, bovine, and chicken (no identity at the N- and C-terminus because the dog sequence misses these sections). Smaller font indicates amino acids not conserved in chicken. Underlined amino acids indicate those at the surface or important based on crystal structure. * indicates glycosylation site.

The present invention is based, in part, on the inventors' observation that anti-intestinal alkaline phosphatase antibodies can lower blood phosphate levels by reducing the amount of phytic phosphorous absorbed into the blood pool of an animal. In particular, in an animal model in which the animals have a lowered blood phosphate level when fed a diet containing phytic phosphate but deficient in the readily absorbable inorganic phosphate and supplementing the diet with vitamin D increases the lowered blood phosphate level, the inventors observed that administering anti-intestinal alkaline phosphatase antibodies to the animals reduced the increased blood phosphate levels caused by vitamin D. The present invention provides new tools for reducing phosphate absorption in a human and non-human animal subject such as a kidney disease patient who consumes a diet containing phytic acid or phytate and needs to take a vitamin D compound (e.g., 1α,25-dihydroxyvitamin $D_3$) for maintaining calcium homeostasis or other purposes wherein the vitamin D compound renders phytic phosphate in the diet available for absorption.

The inventors' studies disclosed herein demonstrate that anti-intestinal alkaline phosphatase antibodies are effective in reducing blood phosphate levels increased by vitamin D despite several pieces of evidence in the prior art suggesting the contrary. First, the prior art suggests that a mechanism independent of intestinal alkaline phosphatase is the reason that vitamin D (1α,25-dihydroxyvitamin $D_3$) increases the blood phosphate level because the addition of vitamin D to an inorganic phosphate deficient diet increases blood phosphate levels in both animals such as rats in which vitamin D increases intestinal alkaline phosphatase activity and animals such as chickens in which vitamin D has no effect on intestinal alkaline phosphatase activity (Biehl and Baker, J Nutr 1997, 127:2054-2059; and Pileggi et al, Arch. Biochem. Biophys. 1995, 58:194-204). Secondly, intestinal alkaline phosphatase is associated with the intestinal brush border membrane (Nakano et al., Arch Histol Cytol 2001, 64:483-491). Prior art suggests that an anti-intestinal alkaline phosphatase antibody would not be effective for blocking intestinal alkaline phosphatase activity in vivo because the intestinal brush border membrane is coated with a mucus layer permeable only to low molecular weight solutes but not to large macromolecules (e.g., antibodies/proteins) in order to protect the mucosal surface from degradation by proteolytic enzymes in the intestinal lumen (Atuma et al, Am J Physiol Gastrointest Liver Physiol 2001, 280:922; and M. Mantle and A. Allen, 1989, Gastrointestinal mucus, pp 202-229 in Gastrointestinal Secretions, J. S. Davison, ed., Butterworth and Co., Great Britain). In addition, it is uncertain whether a particular antibody administered orally can survive the acidic environment in the stomach and remain active. Despite the above prior art evidence to the contrary, the inventors show here that anti-intestinal alkaline phosphatase antibodies can be used to reduce blood phosphate levels increased by vitamin D. Without intending to be limited by theory, the inventors believe that the anti-intestinal alkaline phosphatase antibodies reduce phosphate absorption by binding to intestinal alkaline phosphatase to interfere with the interaction between the enzyme and its substrate (phytic acid/phytate) that would otherwise catalyzes phosphate release.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are now described.

In describing the embodiments and claiming the invention, the following terminology are used in accordance with the definitions set forth below.

As used herein, "antibody" includes an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term also includes bivalent or bispecific molecules, diabodies, triabodies, and tetrabodies. Bivalent and bispecific molecules are described in, e.g., Kostelny et al., J Immunol 1992, 148:1547; Pack and Plückthun, Biochemistry 1992, 31:1579;

Zhu et al., Protein Sci 1997, 6:781; Hu et al., Cancer Res. 1996, 56:3055; Adams et al., Cancer Res. 1993, 53:4026; and McCartney et al., Protein Eng. 1995, 8:301. The term "antibody" also includes antigen binding forms of antibodies such as fragments with antigen-binding capability (e.g., Fab', F(ab')$_2$, Fab, Fv and rIgG). The term also refers to recombinant single chain Fv fragments (scFv). In addition, the term "antibody" encompasses an antibody having a stabilizing group covalently linked thereto to make the antibody more stable. Antibodies with an affinity Kd of $10^{-4}$ M or less can be employed in the present invention. Preferably, antibodies with an affinity Kd of $\leq 10^{-5}$ M or $\leq 10^{-6}$ M are employed. More preferably, antibodies with an affinity Kd of $\leq 10^{-7}$ M, $\leq 10^{-8}$ M, or $\leq 10^{-9}$ M are employed.

As used herein, the term "hyperphosphatemia" is used broadly to describe a condition in a subject wherein serum phosphate is present at a concentration above the medically accepted normal range.

As used herein, the term "attenuate" or "prevent" means achieving a therapeutic benefit or a prophylactic benefit. By therapeutic benefit, we mean amelioration or eradication of the underlying disorder being treated. For example, in a subject having hyperphosphatemia, therapeutic benefit includes amelioration or eradication of the underlying hyperphosphatemia. Also, a therapeutic benefit includes amelioration or eradication of one or more of the pathophysiological symptoms associated with the underlying disorder, such that an improvement is observed in the subject, notwithstanding that the subject may still be afflicted with the underlying disorder. For example, in a patient suffering from renal insufficiency and/or hyperphosphatemia, a therapeutic benefit refers to not only a decrease in the patient's serum phosphate level but also an improvement in the patient with respect to other disorders that accompany renal failure and/or hyperphosphatemia such as ectopic calcification and renal osteodystrophy. For prophylactic benefit, an antibody according to the present invention is administered to a patient at risk of developing hyperphosphatemia or to a patient reporting one or more of the pathophysiological symptoms of hyperphosphatemia even though a diagnosis of hyperphosphatemia may not have been made. For example, an antibody according to the present invention can be administered to a patient with chronic kidney disease where hyperphosphatemia has not been diagnosed. Prophylactic benefit includes prevention or delay of hyperphosphatemia.

As used herein, an effective amount of an antibody is an amount that lowers serum phosphate in a subject having hyperphosphatemia, prevents serum phosphate from rising in a subject having or at risk of having hyperphosphatemia, or reduces the absorption of phosphate from food which can be measured, for example, by increased fecal phosphate or by lowered or stabilized serum phosphate level.

As used herein, "kidney disease" refers to any disease or disorder that affects the function of the kidneys including those diseases of the kidney that result in poor phosphate filtration and includes diseases that affect blood supply to the kidney, as well as functional and structural defects in the kidneys. Examples of kidney disease include, but are not limited to, end stage renal disease, acute renal failure, chronic renal failure, polycystic kidney disease, chronic kidney disease (e.g., stage I, II, III, IV, or V chronic kidney disease as classified under the National Kidney Foundation Kidney Disease Outcomes Quality Initiative Clinical Practice Guidelines, which manifests as renal insufficiency and in later stages renal failure), acute tubular necrosis (e.g., renal artery stenosis), infections that reduce kidney function (e.g., septicemia or kidney infection such as acute pyelonephritis), kidney transplantation rejection, and urinary tract obstruction.

As used herein, the term "Vitamin D" refers broadly to the organic compounds named Vitamin $D_2$, Vitamin $D_3$, Vitamin $D_4$, etc., and to their metabolites and hormonal forms that influence calcium and phosphate homeostasis. Examples of vitamin D compounds include, but are not limited to, vitamin $D_2$ (ergocalciferol), 25-hydroxyvitamin $D_2$, $1\alpha,25$-dihydroxyvitamin $D_2$, vitamin $D_3$ (cholecalciferol), 25-hydroxyvitamin $D_3$, $1\alpha,25$-dihydroxyvitamin $D_3$, an analog of any of the forgoing or which can substantially occupy the intracellular vitamin D receptor, and those described in Bouillon et al., Endocrine Reviews 1995, 16: 200-257, which is herein incorporated by reference in its entirety. Vitamin D compounds also include those that are currently commercially available or in clinical trials including, but not limited to, 19-nor-$1\alpha,25$ dihydroxyvitamin $D_2$ (Paricalcitol), $1\alpha$-hydroxyvitamin $D_2$ (Doxercalciferol), $1\alpha$-hydroxyvitamin $D_3$ (Alfacalcidol), investigational drugs from Leo Pharmaceutical including EB 1089 (Seocalcitol), KH 1060 (20-epi-22-oxa-24a,26a,27a-trihomo-$1\alpha,25$-dihydroxy-$D_3$), MC 1288 and MC 903 (Calcipotriol), Roche Pharmaceutical drugs that include 1,25-dihydroxy-16-ene-$D_3$, 1,25-dihydroxy-16-ene-23-yne-$D_3$, and 25-dihydroxy-16-ene-23-yne-$D_3$, Chugai Pharmaceuticals 22-oxacalcitriol (22-oxa-$1\alpha,25$-dihydroxy-$D_3$), $1\alpha$ hydroxy $D_5$ from the University of Illinois, drugs from the Institute of Medical Chemistry-Schering AG that include ZK 161422 and ZK 157202.

In one aspect, the present invention relates to a method for reducing phosphate absorption in a human or non-human animal subject wherein the subject consumes a diet containing phytic acid or phytate and either has or is at risk of developing hyperphosphatemia. The method includes the step of administering orally to the subject an anti-intestinal alkaline phosphatase antibody in an amount effective to reduce or maintain the serum phosphate concentration in the subject. The method may further include the step of observing a decrease or stabilization of the serum phosphate concentration. For example, the serum phosphate concentrations before and after the antibody treatment can be measured and compared.

The method disclosed here can be used to attenuate or prevent hyperphosphatemia. In some embodiments, the serum phosphate concentration is reduced to or maintained at a level of or lower than about 150%, 125%, 120%, 115%, 110%, or 105% of a maximum physiological serum phosphate concentration in the accepted normal range. In some embodiments, the serum phosphate concentration is reduced to or maintained at a level within the normal range. For a human subject, the maximum high-normal serum phosphate concentration is 5.0 mg/dl. In a preferred embodiment, the serum phosphate concentration is reduced to or maintained at 5.5 mg/dl or lower or 5.0 mg/dl or lower in a human subject.

Patients at risk of developing or that have developed hyperphosphatemia include, but are not limited to, patients with: vitamin D intoxication from excessive intake of vitamin D compounds; excessive phosphate intake such as excessive use of phosphate-containing laxatives or enemas; renal disease or insufficiency such as renal failure, either acute or chronic, as described herein; primary hypoparathyroidism; PTH resistance states such as syndromes of tubular resistance to PTH including the various types of pseudohypoparathyroidism (1a, 1b, 1c, and 2) or severe hypomagnesemia, which impairs PTH secretion and causes peripheral PTH resistance; and/or conditions in which intracellular phosphate shifts to the extracellular space, such as rhabdomyolysis, tumor lysis, insulin deficiency or acute acidosis.

In some embodiments, the method of the present invention is applied to reduce phosphate absorption in a human or non-human subject that has a kidney disease, receives a vitamin D compound (e.g., 1α,25-dihydroxyvitamin $D_3$), or both.

The amino acid sequences of intestinal alkaline phosphatase from various species are known. For example, the amino acid sequences of the human intestinal alkaline phosphatase (SEQ ID NO:1), mouse intestinal alkaline phosphatase (SEQ ID NO:2), rat type I intestinal alkaline phosphatase (SEQ ID NO:3), and rat type II intestinal alkaline phosphatase (SEQ ID NO:4) can be found at NCBI GenBank Accession numbers AAA51703, AAA37873, AAF36717, and NP_073171, respectively. The percent identity between the different intestinal alkaline phosphatases listed above is high (≥76.5%).

In some embodiments, antibodies that bind to an epitope within the following intestinal alkaline phosphatase fragments are used to practice the present invention: amino acids 72-79, 83-90, 123-130, 181-188, 226-233, 260-267, 271-278, 312-319, 363-370, 383-390, or 446-453 of the human intestinal alkaline phosphatase (SEQ ID NO:1); fragments of the mouse intestinal alkaline phosphatase (SEQ ID NO:2) that correspond to the above human intestinal alkaline phosphatase fragments; fragments of the rat type I intestinal alkaline phosphatase (SEQ ID NO:3) that correspond to the above human intestinal alkaline phosphatase fragments; or fragments of the rat type II intestinal alkaline phosphatase (SEQ ID NO:4) that correspond to the above human intestinal alkaline phosphatase fragments. Corresponding fragments can be readily identified by any alignment program familiar to one of ordinary skill in the art. For example, Gapped BLAST can be used as described in Altschul et al. (*Nucleic Acids Res.* 25, 3389-3402, 1997). Gapped BLAST is available at the NCBI website. When utilizing Gapped BLAST program, the default parameters of the program can be used.

In a preferred embodiment, antibodies that bind to an epitope within one of the following human intestinal alkaline phosphatase (SEQ ID NO:1) fragments are used to practice the present invention: amino acids 72-79, 181-188, 226-233, 260-267, 271-278, 383-390, or 446-453. In another preferred embodiment, antibodies that bind to an epitope within one of the following human intestinal alkaline phosphatase (SEQ ID NO:1) fragments are used to practice the present invention: amino acids 83-90, 181-188, 226-233, or 260-267.

It is well within the capability of one of ordinary skill in the art to make an anti-intestinal alkaline phosphatase antibody such as an IgY antibody or an antibody that binds to an epitope within an intestinal alkaline phosphatase fragment. In some embodiments, the antibody employed in the method is derived from an egg (e.g., egg yolk), in particular from an avian egg such as a chicken egg. The method of Polson, A., M. B. von Wechmar and M. H. van Regenmortel, "Isolation of Viral IgY Antibodies from Yolks of Immunized Hens," Immunological Communications 9:475-493 (1980), incorporated herein by reference in its entirety, can be used to produce a preparation of egg-yolk antibodies. Laying hens can be inoculated with an intestinal alkaline phosphatase or an immunogenic fragment thereof. Preferably, a suitable adjuvant is administered in conjunction with the inoculation to enhance the immunization. An adjuvant useful for this purpose is a water-in-oil emulsion adjuvant such as complete Freund's adjuvant. The intestinal alkaline phosphatase or an immunogenic fragment thereof causes the hens to produce anti-intestinal alkaline phosphatase antibodies which are passively transferred into the egg yolk of eggs laid by the hens.

Egg yolks or whole eggs containing the antibody can be collected and homogenized to form an emulsion. The resulting emulsion can be dried to form a powder containing the antibody. This powder can then be formulated in a manner appropriate for oral administration and then administered orally to a human or non-human animal subject. The preparation may be administered orally as a diet or food supplement.

Antibodies of any isotype class or subclass (e.g., IgY, IgG, IgM, IgD, IgA, IgE, IgG1, IgG2, IgG3, IgG4, IgA1 and IgA2) as well as fragments thereof (whether produced by enzymatic or chemical digestion of such antibodies) and preparation of such antibodies by synthetic means or by expression of gene sequences encoding such antibodies or fragments thereof are contemplated. In one embodiment of IgY, antibodies in the egg yolks of an avian animal (e.g., chickens, pheasants, ducks, turkeys, geese and the like) are used to practice the present invention (see e.g., U.S. Pat. Nos. 5,080,895, 5,989,584 and 6,213,930, each of which is herein incorporated by reference in its entirety). Commercially available egg antibody purification kits, such as EGGstract® IgY Purification Systems (Promega; Madison, Wis.) or Eggcellent® Chicken IgY Purification (Pierce Biotechnology, Inc.; Rockford, Ill.), can be used to purify the antibodies. Antibodies can also be purified based on their affinity for peptides or protein fragments using standard means for affinity purification. Alternatively, eggs, egg yolks or dried egg yolk powder containing the antibodies can be mixed with a food directly for oral consumption or easily introduced into a pill, tablet, or capsule. Genes encoding such antibodies can also be identified using such antibodies through well established molecular cloning or phage display techniques to give rise to whole or partial monoclonal forms of such antibodies which could be used alone or in combination.

Compositions containing anti-intestinal alkaline phosphatase antibodies according to the present invention may be dosed, e.g., once, twice or three times a day. Dosing may optionally be subdivided in a manner in which a portion of the prescribed dose is ingested prior to consumption of food or beverages, another portion is ingested together with food or beverages, and yet other portions are ingested close in time after ingestion of food or beverages. The active ingredients can be administered by the oral route as particles or powder sprinkled or distributed on, or in, food; or dissolved or suspended in beverages; or provided in pharmaceutical solid dosage forms, such as tablets, capsules, and powders, or in liquid dosage forms, such as elixirs, syrups, and suspensions. In some embodiments, the antibody is administered with food or close in time (i.e. within about one hour before or after) to the consumption of a food having dietary phosphate. In some embodiments, the antibody is administered concomitantly with a phosphate binder.

Exemplary pharmaceutical compositions according to the present invention comprise IgY and optionally egg components, or IgY and optionally egg yolk components, optionally with additional stabilizers or pharmaceutically acceptable carriers. Whole eggs, or egg yolks, or egg yolks from which lipids are partially or mostly removed may be emulsified, optionally mixed with an encapsulation compound or lyoprotectant, and subjected to spray-drying or freeze-drying to form a powder.

Yolk antibodies can be partially purified, e.g., to remove large quantities of lipid. See Camenisch C et al., FASEB J. 1999, 13:81-88; Akita E & Nakai S, J. Immunol. Methods 1993, 160:207-214, each of which is incorporated herein by reference as if set forth in its entirety; as well as U.S. Patent Publication No. 2004/0087522, incorporated herein by reference as if set forth in its entirety.

Capsules or tablets may contain a controlled-release formulation as may be provided in a dispersion of active compound in hydroxypropyl methylcellulose or related material known to alter the kinetics of release of the active agent. Solid dosage forms can be manufactured as sustained release products to provide for continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Stabilizers are protective agents that maintain the binding activity of the antibody under denaturing conditions, such as heat or acid. The stabilizer does not inhibit interaction of the antibodies with the target antigen, so that the desired biological effect is also maintained. Exemplary stabilizers include egg white, albumin or saccharide compounds. Preferably, the saccharide compound is present at about 5% to 30% of whole egg liquid (by weight), and more preferably in the amount of 10% to 20% of the whole egg liquid (by weight). The antibody is mixed with a saccharide compound in a liquid suspension and the suspension is then dried to produce a solid that contains the protein and the saccharide. Saccharide compounds useful as stabilizers include monosaccharides, disaccharides, polysaccharides, alkylated monosaccharides, alkylated disaccharides, alkylated polysaccharides, monosaccharide alcohols and alkylated monosaccharide alcohols. Preferably, such saccharide compounds are composed of or based on monosaccharide units of 5 or 6 carbons. Monosaccharides are single sugar residues having the formula $(CH_2O)n$ wherein n is 3 or more. Examples of monosaccharides include but are not limited to glucose, ribose, fructose, galactose, talose, arabinose, fucose, mannose, xylose and erythrose. Monosaccharides in all isomeric forms such as α-isomers, β-isomers, D-isomers and L-isomers have activity. Disaccharides are molecules with two monosaccharide residues joined together by a glycosidic bond. Examples of disaccharides that can be used in the present invention include but are not limited to trehalose, maltose, sucrose, lactose, maltose and lactulose. Polysaccharides are molecules with three or more monosaccharides linked together in linear, unbranched chains or branched chains. Starch, glycogen and cellulose are examples of polysaccharides having hundreds or even thousands of monosaccharide residues. Starch can contain either linear, unbranched chains (amylose) or highly branched chains (amylopectin). Glycogen contains branched chains and cellulose contains linear, unbranched chains. Alkylated monosaccharides, alkylated disaccharides and alkylated polysaccharides are monosaccharides, disaccharides and polysaccharides with at least one of the hydrogen groups substituted by an alkyl group. Monosaccharide alcohols are acyclic polyols that contain three or more hydroxyl groups. They can be formed by converting the ketone or aldehyde groups of the monosaccharides to hydroxyl groups. Examples of monosaccharide alcohols include but are not limited to glycerine, mannitol, sorbitol, xylitol, lactitol, isomalt, maltitol, and hydrogenated starch hydrolysates. Alkylated monosaccharide alcohols are monosaccharide alcohols with at least one of the hydrogen groups substituted by an alkyl group.

Antibodies can also be attached to a matrix (polymeric or non-polymeric) substrate for the purposes of enhancing the efficacy or stability of the antibodies and then administered.

The invention will be more fully understood upon consideration of the following non-limiting examples.

Example 1

Reducing Serum Phosphate Levels Increased by Vitamin $D_3$

Materials and Methods
Animals Used for Antibody Production:

Single Comb White Leghorn laying hens were used for antibody production (3 hens per peptide antigen). Each peptide antigen (see Table 1 for sequence and FIG. 1 for sequence and other features) was prepared by conjugating peptide to bovine gamma globulin using standard glutaraldehyde procedure. In some studies, whole enzymes were purchase and used without conjugation. In preparations using whole enzymes (Table 2), vaccine preparations and injection schedules were identical to those described for the conjugated peptides (see below).

TABLE 1

The amino acid sequence of peptides used to produce egg antibodies. Amino acid sequences are based on predicted conserved regions of intestinal alkaline phosphatase among animal species. Regions of interest include hydrophilic surface, entrance to the active site, dimmer interface, and metal binding domain.

| Arbitrary Peptide No. (SEQ ID NO) | amino acid sequence (positions in SEQ ID NO: 1) | enzyme location |
|---|---|---|
| 1 (SEQ ID NO: 5) | GPETPLAM (83-90) | surface |
| 2 (SEQ ID NO: 6) | KTYNVDRQ (100-107) | dimer interface |
| 3 (SEQ ID NO: 7) | KANFQTIG (123-130) | |
| 4 (SEQ ID NO: 8) | KQAGKSVG (156-163) | |
| 5 (SEQ ID NO: 9) | HTVNRNWY (181-188) | active site entrance |
| 6 (SEQ ID NO: 10) | MFPMGTPD (226-233) | surface |
| 7 (SEQ ID NO: 11) | EAALRLLS (312-319) | surface |
| 8 (SEQ ID NO: 12) | GRIDHGHH (332-339) | |
| 9 (SEQ ID NO: 13) | FGGYTLRG (383-390) | active site entrance |
| 10 (SEQ ID NO: 14) | LSSETHGG (446-453) | active site entrance |
| 24 (SEQ ID NO: 15) | QAAEALDA (34-41) | surface |
| 25 (SEQ ID NO: 16) | RILKGQKN (72-79) | |
| 26 (SEQ ID NO: 17) | QHASPAGT (171-178) | active site entrance |
| 27 (SEQ ID NO: 18) | DADMPASA (190-197) | |
| 28 (SEQ ID NO: 19) | HQGAWYVW (260-267) | surface, metal binding domain |
| 29 (SEQ ID NO: 20) | ELMQASLD (271-278) | surface |
| 30 (SEQ ID NO: 21) | LTSEEDTL (363-370) | |

TABLE 2

Commercially available phosphatase enzymes
used as vaccines for making egg antibodies.

| Enzyme | Source | Vendor |
|---|---|---|
| Placental alkaline phosphatase | human | Biodesign Intl |
| Phytase | fungal (*Aspergillus ficuum*) | Sigma |
| Intestinal alkaline phosphatase | chicken | Worthington |
| Intestinal alkaline phosphatase | calf | Worthington |
| Alkaline phosphatase | microbial (*E. coli*) | Worthington |

Conjugation Preparation:

While the procedure for conjugation of peptides to carrier proteins can vary considerably (a number of kits for conjugation can be obtained from Pierce Scientific), as well as the nature of the carrier proteins, the method used in the studies described in this example involved the use of the glutaraldehyde procedure for conjugation of the desired peptide to the carrier protein bovine gamma globulin (BgG). BgG (4 mg) in 0.8 ml of 0.1 M sodium acetate buffer (pH=7) was mixed with 4 mg of the desire peptide (see Table 1 below). 0.52 ml of 0.02 M glutaraldehyde (in 0.1 M sodium acetate buffer) was added dropwise (to avoid foaming) to the peptide carrier protein mixture. The mixture was stirred for 2 hours. 20 mg glycine was then added to stop the reaction. The mixture was allowed to set for 1 hour and then was dialyzed against phosphate buffered saline (pH=7) overnight (MW=6000-8000). The dialyzed conjugate was then frozen at −80° C. until used.

Vaccine Preparation and Use:

To prepare a vaccine for each hen 0.5 mg of conjugate was diluted to a final concentration of 0.5 ml PBS and mixed with 0.5 ml of Freund's complete adjuvant (first injection) or incomplete adjuvant (booster vaccination) to form a water in oil emulsification capable of holding a bead when dripped on ice water. The hen was then injected in four sites (each leg and each breast) with 0.25 ml of the vaccine emulsion intramuscularly. The booster injection in incomplete adjuvant occurred 7 days later. Each peptide shown in Table 1 was separately conjugated to BgG and injected into 3 laying hens.

Antibody Sample Preparation:

Peak antibodies were achieved by 21 days, hence eggs were collected from day 21 to day 110. In approximately 30 day lots, egg yolks from each hen were separated from whole eggs, mixed and lyophilized. Dried egg yolk powder containing the antibody was stored at room temperature until use in animal feeding studies. Eggs from each hen can also be collected, yolks separated and IgY polyethylene purified using procedures described in Polson et al., Immunol. Commun. 1980, 9:475-493.

Animal Model:

The dietary sources of inorganic phosphate (Pi) are largely mineral phosphates or phosphate from animal tissues and products (milk and eggs). These Pi sources are readily available for absorption by monogastric animals. In diseases where the uptake of phosphorous requires intervention, patients are usually required to avoid these foods and take Pi binders. While this is a useful strategy in reducing the absorption of Pi, patients taking alternative food (e.g., plant based foods) during the treatment of diseases such as end stage renal failure is exposed to another source of phosphate that may serve as a pool of Pi for absorption. Phytic phosphorous (PP) represents 70-80% of all phosphorous in plant based foods. PP is normally unavailable for absorption in monogastric animals when consumed and is excreted with the fecal waste.

The animal model used in this example is the chicken model in which chickens were fed a Pi deficient diet that resulted in low serum phosphate level. Providing 1α-hydroxyvitamin $D_3$ to the chickens fed the Pi deficient diet raised the serum phosphate level. Therefore, this model can be used to test whether anti-intestinal alkaline phosphatase antibodies would be effective in reducing increased serum phosphate levels from a phytic origin caused by 1α-hydroxyvitamin $D_3$.

Animal Experiment:

The chicken model used in this study was described by Biehl and Baker, J. Nutr. 1997, 127:2054-2059 with the exception of antibodies to intestinal alkaline phosphatas peptides and commercial enzymes. The negative control used in this study was a Pi deficient diet (Pi=inorganic phosphate which are largely mineral phosphates or phosphate from animal tissues and products such as milk and eggs), where the dietary phosphorous used was phytic phosphate. As shown in the results below, this dietary treatment resulted in low plasma phosphorous. The positive control was the same diet as the negative control, but supplemented with 1α-hydroxyvitamin $D_3$ (20 µg/kg diet, Sigma). As shown in the results below, this dietary treatment increased blood phosphorous levels, through the liberation of phytic phosphorous, in comparison to the negative control. All the remaining dietary treatments were the positive control plus the antibody (1 g of dried egg yolk powder produced as described above) (17 to peptides and 5 to complete enzymes). The negative and positive controls were fed 1 g/kg diet of dried yolk powder from hens injected with the adjuvant. These egg yolk powders lacked specific antibodies.

A total of 24 treatments were used (negative control, positive control, positive control plus each of the 17 anti-peptide antibodies, and the positive control plus each of the 5 anti-phosphatase enzyme antibodies). Six one-day old male Single Comb White Leghorn chicks were assigned to each of the dietary treatments. Chicks were fed the dietary treatments for 10 days, weighed, then blood sampled for determining plasma phosphorous concentration using a Roche/Hitachi analyzer (based on the reaction of phosphate with ammonium molybdate to form ammonium phosphomolybdate without reduction). Chicks were euthanized and the right tibiotarsus of each chick was collected, dried, ether extracted, and ashed for the determination of bone mineral content of fat free, dried bone.

Since the preplanned comparison of differences was to test whether the antibody reduced the endpoint relative to the positive control, statistical analysis was conducted comparing the parameter measured and the positive control using a t-test. Values were reported as significant if *$p<0.1$ or **$p<0.05$.

Results

Antibodies directed to a number of sites on intestinal alkaline phosphatase were effective at preventing an increase in plasma phosphorous caused by active vitamin D (Table 3). Antibodies to the surface of the enzyme and to the entrance of the catalytic site appeared to be effective (Table 3).

TABLE 3

Plasma phosphorous of chickens fed anti-intestinal alkaline
phosphatase antibodies in the presence of active vitamin $D^1$

| Dietary treatment | plasma phosphate (mg/dL) | Standard error |
|---|---|---|
| Pi Deficient | 3.92 | 0.35 |
| Active Vitamin $D^2$ | 6.70 | 0.51 |
| peptide 1** | 5.55 | 0.36 |

TABLE 3-continued

Plasma phosphorous of chickens fed anti-intestinal alkaline phosphatase antibodies in the presence of active vitamin D[1]

| Dietary treatment | plasma phosphate (mg/dL) | Standard error |
|---|---|---|
| peptide 2 | 5.77 | 0.51 |
| peptide 3* | 4.95 | 0.87 |
| peptide 4 | 6.77 | 1.06 |
| peptide 5** | 4.65 | 0.78 |
| peptide 6** | 4.88 | 0.18 |
| peptide 7* | 5.35 | 0.73 |
| peptide 8 | 5.80 | 0.57 |
| peptide 9** | 4.93 | 0.54 |
| peptide 10** | 4.28 | 0.46 |
| peptide 24 | 5.38 | 0.58 |
| peptide 25** | 4.57 | 0.69 |
| peptide 27 | 5.73 | 0.98 |
| peptide 28** | 4.70 | 0.35 |
| peptide 29** | 4.97 | 0.50 |
| peptide 30** | 5.52 | 0.32 |

[1]One day old leghorn chicks (n = 6) were fed a Pi deficient diet containing phytic phosphorous with the addition of 1α-hydroxyvitamin $D_3$ alone (active vitamin D, 20 μg/kg diet) or the addition of 1α-hydroxyvitamin $D_3$ plus an egg antibody (1 g/kg diet of dried egg yolk antibody powder) to peptides in intestinal alkaline phosphatase. Plasma phosphorous was measured after 10 days of feeding the diet.
[2]Chickens on the active vitamin D diet (1α-hydroxyvitamin $D_3$) had increased plasma phosphorous relative to the chickens on Pi deficient diet (p = 0.0004).
*or **Chickens fed the active vitamin D diet (1α-hydroxyvitamin $D_3$) supplemented with antibody to the indicated peptide had reduced plasma phosphorous relative to active vitamin D alone treatment at *p < 0.1 or **p < 0.05.

Antibodies to chicken intestinal alkaline phosphatase and *E. coli* alkaline phosphatase but not phytase, calf intestinal alkaline phosphatase or human placental alkaline phosphates were effective at reducing plasma phosphorous levels increased by vitamin D (Table 4).

TABLE 4

Plasma phosphorous of chickens fed anti-intestinal alkaline phosphatases (IAP) antibodies in the presence of active vitamin D[1]

| Dietary treatment | Plasma phosphate (mg/dL) | Standard error |
|---|---|---|
| Pi Deficient | 3.92 | 0.35 |
| Active vitamin D[2] | 6.70 | 0.51 |
| Human placenta AP | 5.20 | 0.60 |
| Phytase | 5.97 | 0.60 |
| Chicken IAP** | 4.73 | 0.29 |
| Calf IAP | 3.97 | 0.47 |
| *E. coli* AP** | 4.67 | 0.55 |

[1]One day old leghorn chicks (n = 6) were fed a Pi deficient diet containing phytic phosphorous with the addition of 1α-hydroxyvitamin $D_3$ alone (active vitamin D, 20 μg/kg diet) or the addition of 1α-hydroxyvitamin $D_3$ plus an egg antibody (1 g/kg diet of dried egg yolk antibody powder) to phosphatase enzymes. Plasma phosphorous was measured after 10 days of feeding the diet.
[2]Chickens on the active vitamin D diet (1α-hydroxyvitamin $D_3$) had increased plasma phosphorous relative to the chickens on Pi deficient diet (p = 0.0004).
**Chicks fed the active vitamin D diet (1α-hydroxyvitamin $D_3$) supplemented with antibody to the indicated phosphatase had reduced plasma phosphorous relative to active vitamin D alone treatment at p < 0.05.

Bone ash was also measured in this study. The addition of 1α-hydroxyvitamin $D_3$ increased bone ash by 8% when compared to that of chickens fed the Pi deficient negative control diet (37.4 vs 34.6%, respectively). None of the antibodies to peptides or phosphatases prevented the increase in bone ash associated with 1α-hydroxyvitamin $D_3$. This indicates that blood phosphorous level could be reduced with the antibody without adversely affecting bone mineralization.

The data presented in this example show that antibodies to intestinal alkaline phosphatase and select intestinal alkaline phosphatase peptides can be used to reduce increased flux of phytic phosphorous into the blood pool of an animal. Accordingly, these antibodies can be used to reduce phosphate absorption in patients such as kidney disease patients who are taking vitamin D.

Example 2

Figure 2:
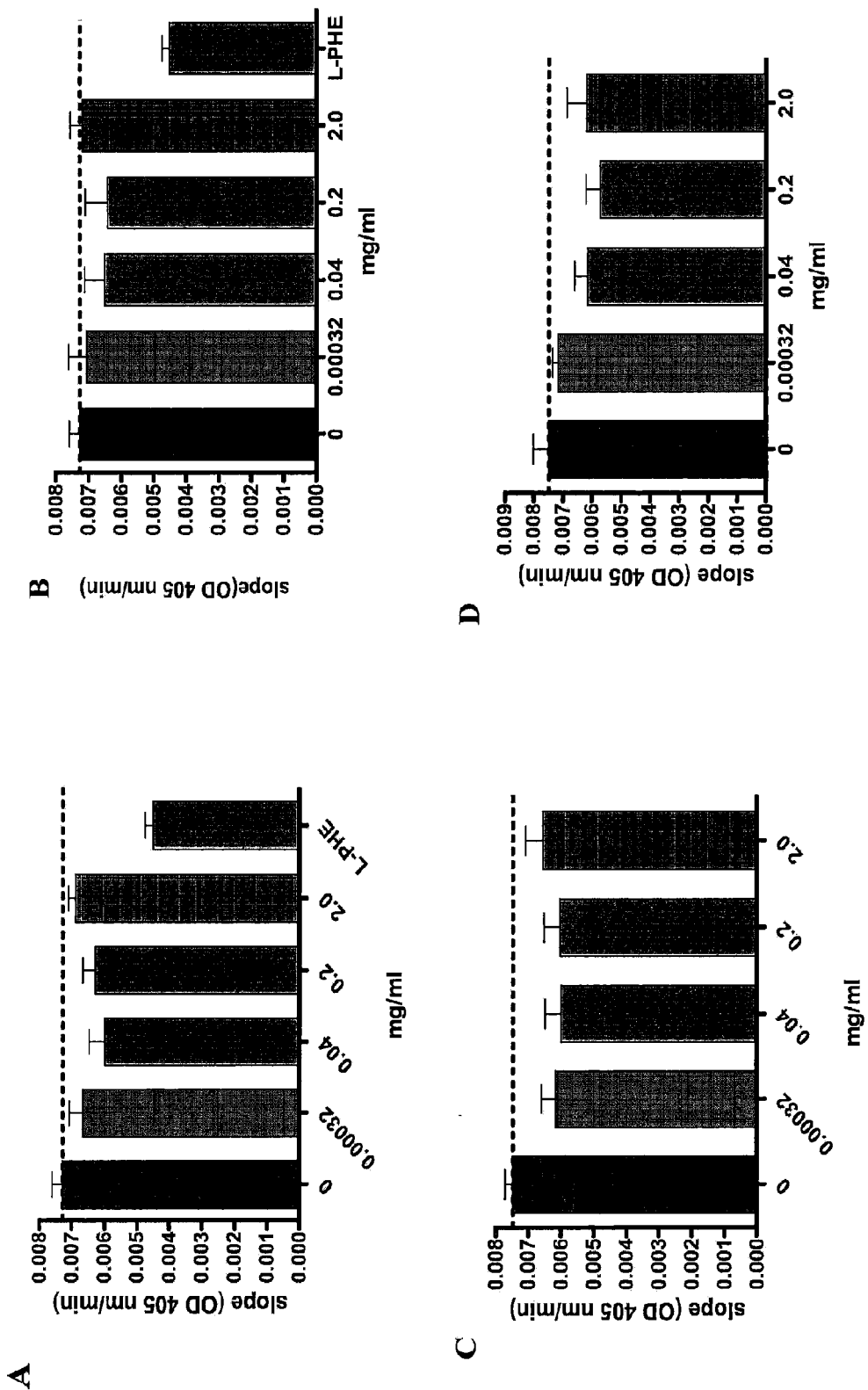
FIG. 2 shows that anti-intestinal alkaline phosphatase antibodies blocked the activity of intestinal alkaline phosphatase activity in vitro. Panels A-I show the effect of anti-intestinal alkaline phosphatase antibodies made with peptides 1, 5, 6, 28, 3, 9, 10, 25, and 29, respectively, on the activity of intestinal alkaline phosphatase of Caco-2 cells. Panels J and K show the effect of egg yolk antibodies obtained before peptide 5 and 6 injection on the activity of intestinal alkaline phosphatase of Caco-2 cells, respectively. The reactions for panels G, H, and I were run at pH=9 while the reactions for all other panels were run at pH=7.4. The x-axis indicates the antibody dilutions and the y-axis indicates the increase in $OD_{405}$ as described in example 2. L-PHE (L-phenylalanine, 5 mM) in panels A and B is a known inhibitor of intestinal alkaline phosphatase and was used as control.
Figure 2:
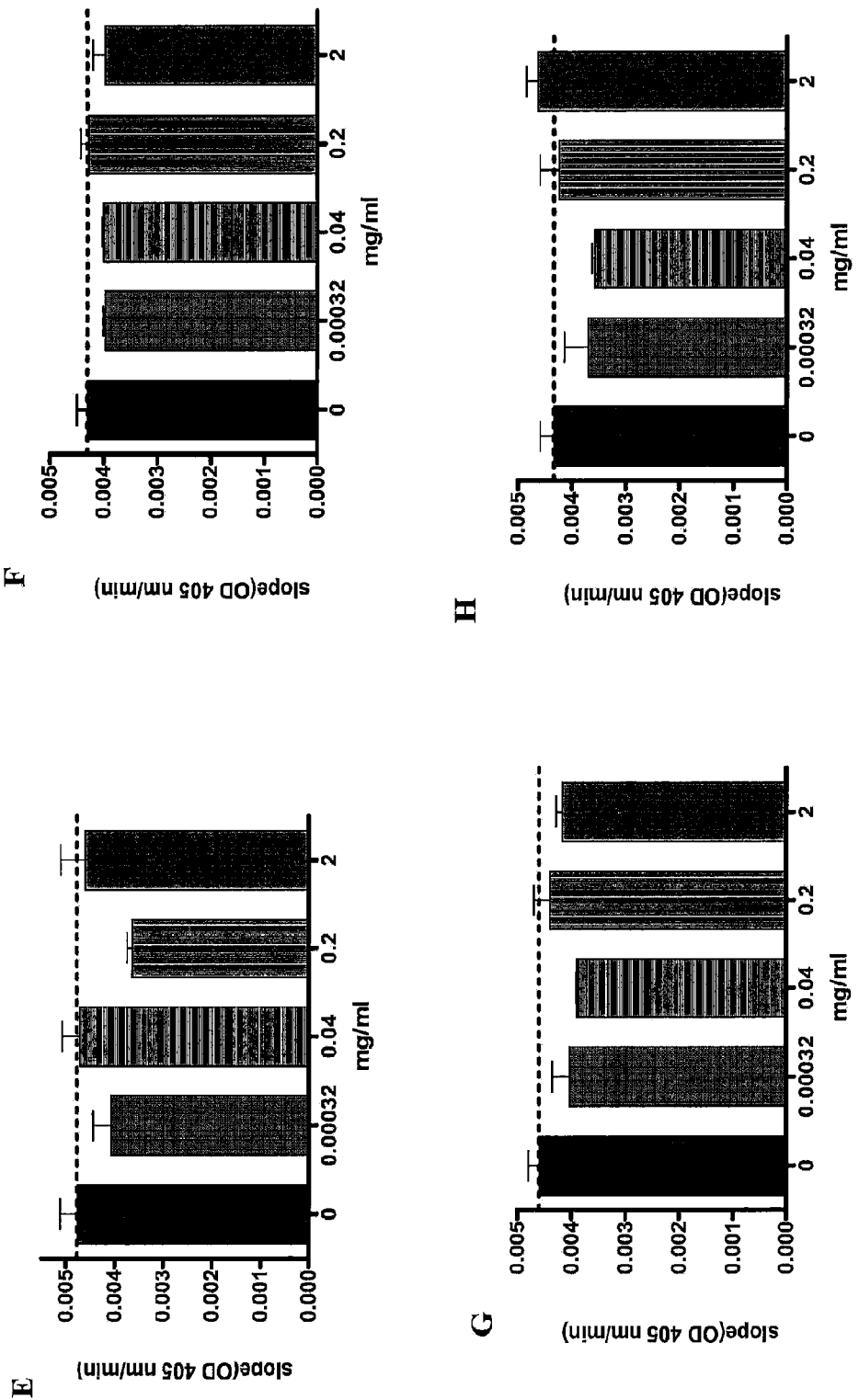
Figure 2:
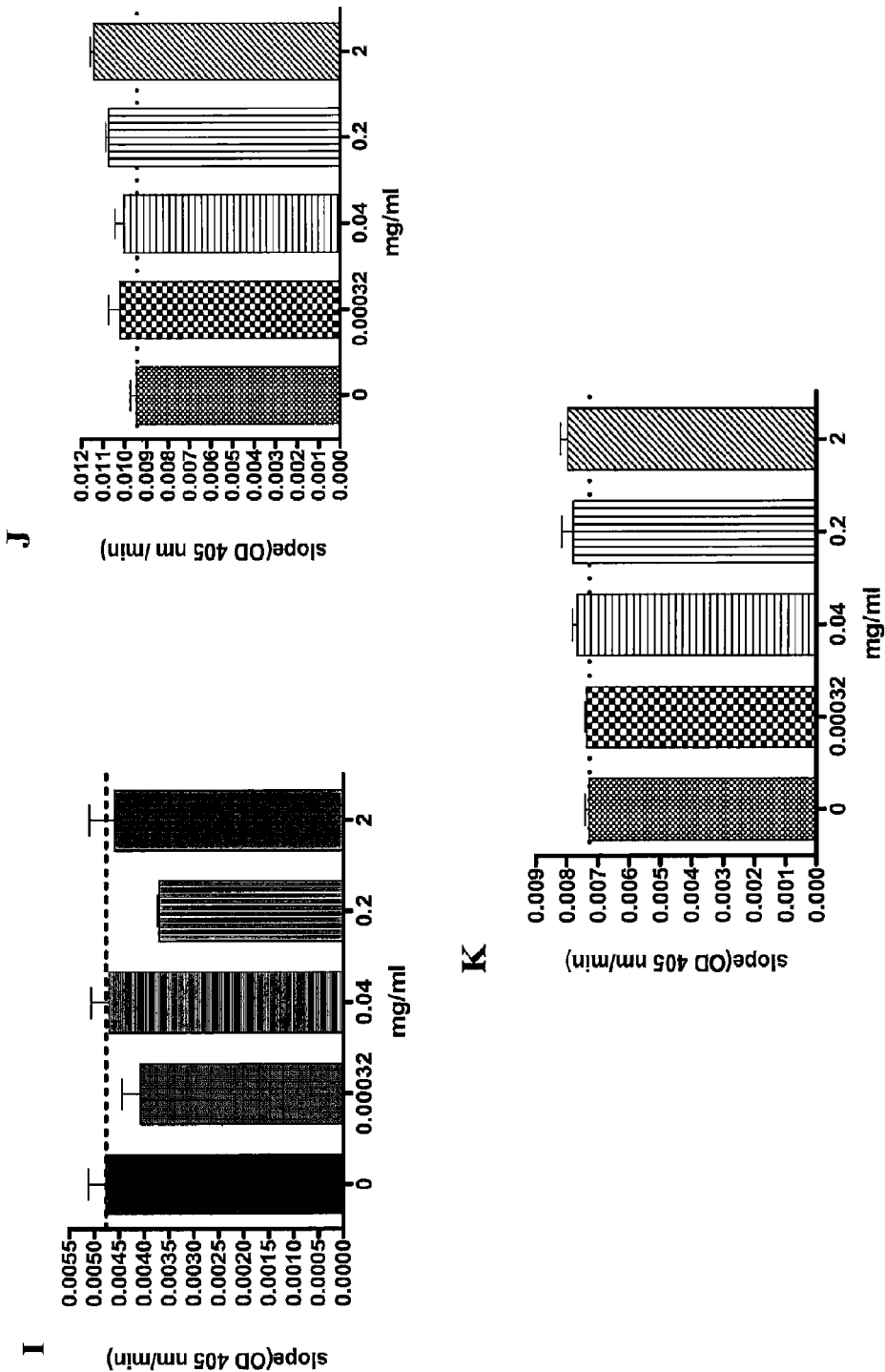
Figure 3:
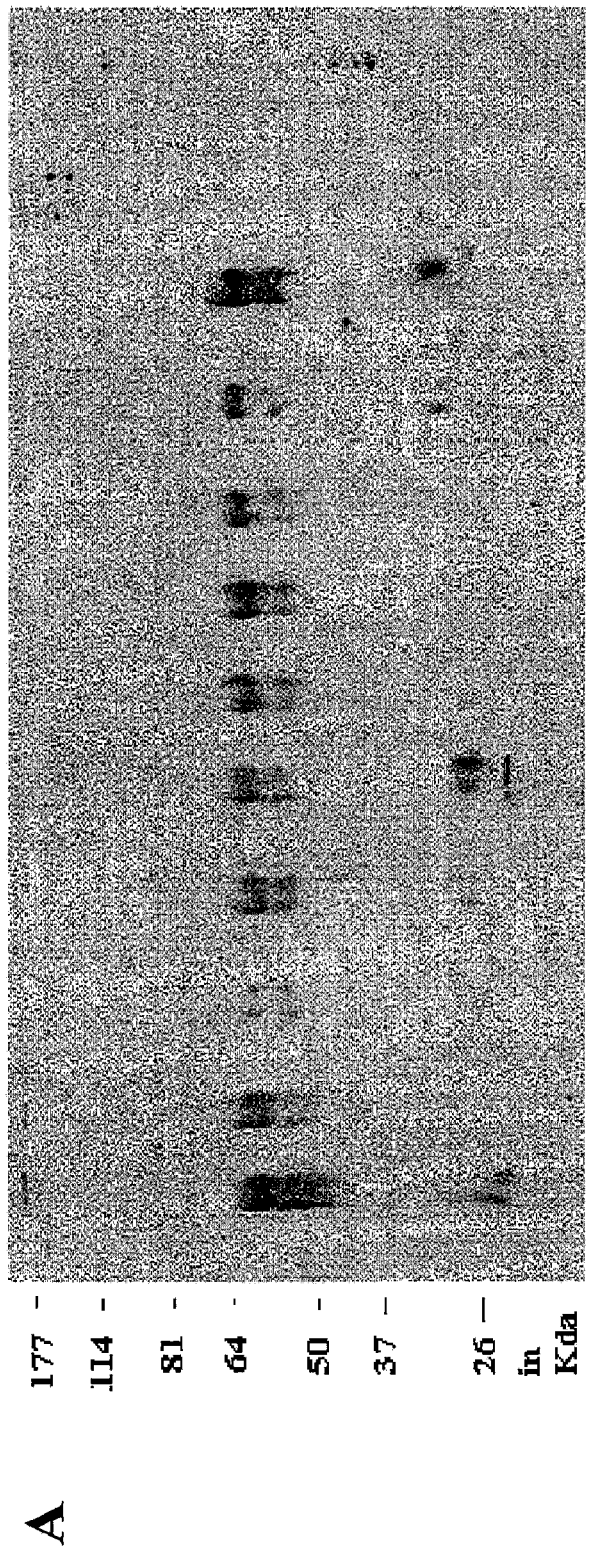
FIG. 3 shows the Western blot of Caco-2 cell intestinal alkaline phosphatase probed with various anti-intestinal alkaline phosphatase antibodies. Molecular weight is shown to the left of the Western blot image. "Ref" indicates a commercial anti-human intestinal alkaline phosphatase antibody. "Ab#" indicates the antibody generated using the particular intestinal alkaline phosphatase peptide as provided in Table 1. "Pre#" indicates egg yolk antibodies obtained before the injection of a particular peptide.
Figure 3:
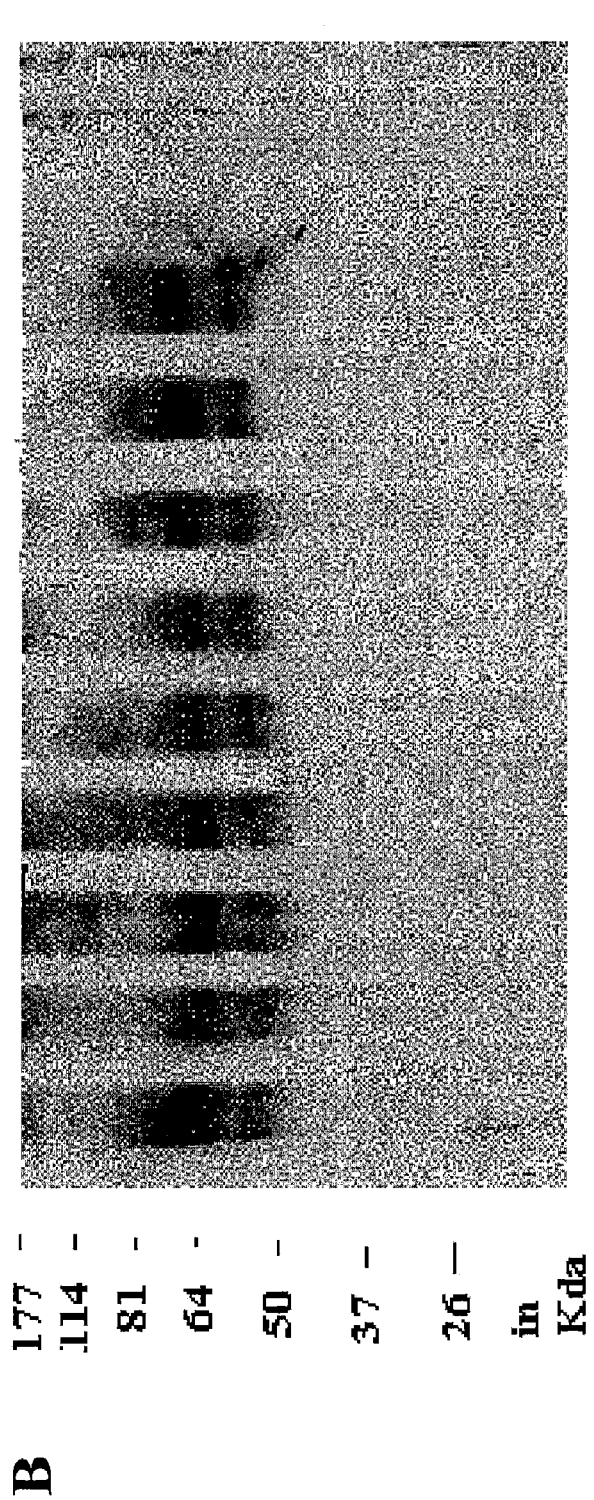

Anti-Intestinal Alkaline Phosphatase Antibodies Bind and Inhibit the Activity of Intestinal Alkaline Phosphatase Materials and Methods
Antibodies:
The production of anti-intestinal alkaline phosphatase antibodies using various intestinal alkaline phosphatase peptides has been described in Example 1 above.
Intestinal Alkaline Phosphatase (IAP) Assay:
Cell extract from Caco-2 C2BBe1 (# CRL-2102, ATCC, a colorectal adenocarcinoma cell line) were obtained from cultures reaching 100% confluency. Cells were resuspended in assay buffer (19 mM Tris-HCl, 2.68 mM KCl, 137 mM NaCl and 0.1% Triton X-100) and were lyzed by sonication in the presence of 0.5 mg/ml of protease inhibitors (Complete, Roche). Lyophilized and PEG precipitated antibodies (egg yolk) were dissolved in 0.9% saline water. 200 μl of antibodies at 0, 2, 1, 0.2, 0.04, 0.08, 0.0016, and 0.00032 mg/ml were mixed respectively with 50 μl of cell extract, 450 μl of assay buffer containing 0.5 mM $MgCl_2$ at the pH 7.4 or pH 9.0 and 300 μl of 1.0 mg/ml p-nitrophenyl phosphate dissolved in 0.2 M Tris Buffer. Enzyme reaction was carried out at 37° C. for 0, 15, 30, 45, 60, 90, 120, 180 min. For each time point, the optical density at 405 nm was measured. The increase of $OD_{405}$ for the incubation containing the antibody was calculated.
Western Blot:
Proteins from human intestine were loaded on a 10% acrylamide gel and run at 120 V for one hour. Proteins were then transferred onto a nitrocellulose membrane using 20 V for 12 hours at 4° C. and exposed to a 1/1000 dilution of primary antibodies (1/500 dilution for antibody #5). After 3 hours the membrane was washed several times and incubated with a 1/5000 dilution of secondary antibody (horseradish peroxidase conjugated) for 90 min. The signal was detected using the Amersham ECL kit.
Results
Anti-intestinal alkaline phosphatase antibodies made using peptides 1, 3, 5, 6, 9, 10, 25, 28, and 29 were tested in vitro for their effects on the activity of intestinal alkaline phosphatase. As shown in FIG. 2, all antibodies tested were able to block the activity of intestinal alkaline phosphatase of Caco-2 cells while the preimmune controls for peptides 5 and 6 did not have any effect on the activity of the phosphatase. Furthermore, Western blot analyses show that all antibodies made using the intestinal alkaline phosphatase peptides as described in example 1 recognized the enzyme while the preimmune controls did not (FIG. 3).

Example 3

Reducing Serum Phosphate Level in Adenine-Induced Uremic Animals

The animal model used in this example is the adenine-induced uremic rat model (see e.g., Yokazawa et al., Nephron 1986, 44:230-234; Katsumata et al., Kid Intl 2003, 64:441-450; and Levi R et al., J Am Soc Nephrol 2006, 17:107-112, each of which is herein incorporated by reference in its entirety).
Rats (e.g., male Sprague Dawley rats approximately 175-250 g, up to 10 rats per group) are fed a control diet or a uremia-inducing adenine diet (e.g., containing 0.75% adenine) for a period of weeks (e.g., 3 to 5 weeks or longer).

In one embodiment, the diet can contain phytic phosphate or both inorganic phosphate and phytic phosphate. Rats fed the adenine diet will develop hyperphosphatemia with level of serum phosphate higher than 4.4 mmol/L. These rats will also develop vitamin $D_3$, (1α-hydroxyvitamin $D_3$ and 1α,25-dihydroxyvitamin $D_3$) deficiency. The daily oral treatment of these rats fed the adenine diet with increasing amount of anti-intestinal alkaline phosphatase antibody such as those described in Example 1 will result in a dose dependent reduction of serum phosphate levels. If these antibodies are given within the first 4 weeks of adenine treatment and thereafter, these anti-intestinal alkaline phosphatase antibodies will prevent, delay or reverse the development of hyperphosphatemia in these rats.

In other groups, rats fed the adenine diet are given a form of vitamin D (e.g., 25-hydroxyvitamin D or derivatives thereof or an active vitamin D agent such as 1α,25-dihydroxyvitamin $D_3$) to prevent or correct active vitamin D deficiency. In one embodiment, the diet can contain phytic phosphate or both inorganic phosphate and phytic phosphate. The vitamin D treatment will make rats more susceptible to hyperphosphatemia and will exacerbate hyperphosphatemia in these rats once developed. Treating these rats receiving vitamin D (e.g., 1α,25-dihydroxyvitamin $D_3$) orally with increasing dose of anti-intestinal alkaline phosphatase antibody such as those described in Example 1 will reduce serum phosphate levels in these rats in a dose dependent manner. If the antibodies are given within the first 4 weeks of adenine treatment and thereafter, these anti-intestinal alkaline phosphatase antibodies will prevent or delay the development or exacerbation of hyperphosphatemia.

Similar experiments can be conducted using other adenine-induced uremic animals such as dogs, pigs, and monkeys.

Example 4

Reducing Serum Phosphate Level in 5/6 Nephrectomized Rats

For 5/6 nephrectomy (see e.g., Cozzolino M et al., Kidney Int. 2003, 64:1653-61), several branches of the left renal artery were ligated and the right kidney excised. 5/6 nephrectomized rats (e.g., male Sprague Dawley rats, approximately 175-250 g, up to 10 rats per group) are fed a high phosphate diet (e.g., 0.9% phosphate). In one embodiment, the diet can contain phytic phosphate or both inorganic phosphate and phytic phosphate. These rats will become uremic weeks after surgery (e.g., 4 to 8 weeks) and develop renal failure, hyperphosphatemia, and active vitamin $D_3$ (1α-hydroxyvitamin $D_3$ and 1α,25-dihydroxyvitamin $D_3$) deficiency. The daily oral treatment of these 5/6 nephrectomized rats fed the high phosphate diet with increasing amount of anti-intestinal alkaline phosphatase antibody such as those described in Example 1 will reduce the serum phosphate level in a dose dependent manner in these rats. If the antibodies such as those described in Example 1 are given within the first few weeks following surgery and thereafter they will either prevent or delay the development of hyperphosphatemia in these rats.

In other groups, 5/6 nephrectomized rats fed the high phosphate diet are given a form of vitamin D (e.g., 25-hydroxyvitamin D or derivatives thereof or an active vitamin D agent such as 1α,25-dihydroxyvitamin $D_3$) to prevent or correct active vitamin D deficiency. However, this treatment will make rats more susceptible to hyperphosphatemia and will exacerbate hyperphosphatemia in these rats once developed. Treating these rats receiving vitamin D (e.g., 1α,25-dihydroxyvitamin $D_3$) orally with increasing dose of anti-intestinal alkaline phosphatase antibody such as those described in Example 1 will reduce the serum phosphate level. If the antibodies are given within the first few weeks of surgery and thereafter, these anti-intestinal alkaline phosphatase antibodies will prevent or delay the development or exacerbation of hyperphosphatemia in these rats.

The present invention is not intended to be limited to the foregoing examples, but to encompass all such modifications and variations as come within the scope of the appended claims.

We claim:

1. A method of reducing phosphorus absorption in a human or non-human subject wherein the subject consumes a diet containing phytic acid or phytate and either has or is at risk of developing hyperphosphatemia, the method comprising the step of:
    administering orally to the subject an anti-intestinal alkaline phosphatase antibody in an amount effective to reduce or maintain the serum phosphorus concentration in the subject, wherein the antibody binds to an epitope of human intestinal alkaline phosphatase within amino acids 72-79, 83-90, 123-130, 181-188, 226-233, 260-267, 271-278, 312-319, 363-370, 383-390, or 446-453 of SEQ ID NO: 1.

2. The method of claim 1, wherein the subject has a kidney disease.

3. The method of claim 2, wherein the kidney disease is selected from the group consisting of end stage renal disease, acute renal failure, chronic renal failure, polycystic kidney disease, chronic kidney disease, acute tubular necrosis, an infection that reduces kidney function and a urinary tract obstruction.

4. The method of claim 1, wherein the subject is receiving a vitamin D compound.

5. The method of claim 1, wherein the antibody binds to the epitope with an affinity of at least $10^{-7}$ M.

6. The method of claim 1, wherein the antibody is an IgY antibody.

7. The method as recited in claim 1, wherein the antibody is obtained from an avian egg.

8. The method as recited in claim 1, wherein the antibody is administered with a phosphate binder.

9. The method of claim 1, wherein the subject is a human subject and the antibody is an anti-human intestinal alkaline phosphatase antibody.

10. The method of claim 1, further comprising the steps of measuring the serum phosphate concentration after the anti-intestinal phosphatase antibody is administered and comparing the comparing the concentration to that before the anti-intestinal phosphatase antibody is administered.

11. A method of reducing phosphate absorption in a human subject who has a kidney disease, receives a vitamin D compound, and consumes a diet containing phytic acid or phytate wherein the vitamin D compound renders the phytic phosphate in the diet available for absorption, the method comprising the step of:
    administering orally to the human subject an anti-human intestinal alkaline phosphatase antibody in an amount effective to reduce or maintain the serum phosphate concentration in the subject, wherein the antibody binds to an epitope of human intestinal alkaline phosphatase within amino acids 72-79, 83-90, 123-130, 181-188, 226-233, 260-267, 271-278, 312-319, 363-370, 383-390, or 446-453 of SEQ ID NO:1.

12. The method as recited in claim 11, wherein the kidney disease is selected from the group consisting of end stage renal disease, acute renal failure, chronic renal failure, polycystic kidney disease, chronic kidney disease, acute tubular necrosis, an infection that reduces kidney function and a urinary tract obstruction.

13. The method of claim 11, wherein the antibody binds to the epitope with an affinity of at least $10^{-7}$ M.

14. The method of claim 11, wherein the antibody is an IgY antibody.

15. The method as recited in claim 11, wherein the antibody is obtained from an avian egg.

16. The method as recited in claim 11, wherein the antibody is administered with a phosphate binder.

17. The method of claim 11, further comprising the steps of measuring the serum phosphate concentration after the anti-intestinal phosphatase antibody is administered and comparing the comparing the concentration to that before the anti-intestinal phosphatase antibody is administered.

\* \* \* \* \*